(12) United States Patent
Lee et al.

(10) Patent No.: US 11,344,280 B2
(45) Date of Patent: May 31, 2022

(54) PROBE APPARATUS, MEDICAL INSTRUMENT COMPRISING SAME, AND CONTROL METHOD OF PROBE APPARATUS

(71) Applicant: SAMSUNG ELECTRONICS CO., LTD., Suwon-si (KR)

(72) Inventors: Jei-young Lee, Yongin-si (KR); Dong-ki Kim, Seoul (KR); Young-hwan Kim, Hwaseong-si (KR); Min-woo Seo, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 304 days.

(21) Appl. No.: 15/759,327

(22) PCT Filed: Oct. 14, 2016

(86) PCT No.: PCT/KR2016/011570
§ 371 (c)(1),
(2) Date: Mar. 12, 2018

(87) PCT Pub. No.: WO2017/065562
PCT Pub. Date: Apr. 20, 2017

(65) Prior Publication Data
US 2018/0249986 A1    Sep. 6, 2018

(30) Foreign Application Priority Data

Oct. 16, 2015 (KR) .................... 10-2015-0144749

(51) Int. Cl.
*A61B 8/00* (2006.01)
*G01S 7/52* (2006.01)
*A61B 8/14* (2006.01)

(52) U.S. Cl.
CPC .............. *A61B 8/4411* (2013.01); *A61B 8/00* (2013.01); *A61B 8/145* (2013.01); *A61B 8/4438* (2013.01);
(Continued)

(58) Field of Classification Search
CPC ..... A61B 8/4411; A61B 8/145; A61B 8/4455; A61B 8/4488; A61B 8/54; A61B 8/58
See application file for complete search history.

(56) References Cited

U.S. PATENT DOCUMENTS

| 5,517,994 A | 5/1996 | Burke et al. |
| 8,143,898 B1 * | 3/2012 | Markoff ................. A61B 6/583 324/522 |

(Continued)

FOREIGN PATENT DOCUMENTS

| JP | H09-292377 | 11/1997 |
| JP | 11-070109 | 3/1999 |

(Continued)

OTHER PUBLICATIONS

International Search Report for PCT/KR2016/011570, dated Feb. 13, 2017, 3 pages.
(Continued)

*Primary Examiner* — Rochelle D Turchen
(74) *Attorney, Agent, or Firm* — Nixon & Vanderhye, P.C.

(57) ABSTRACT

An example medical probe apparatus includes a main body; and a head which is detachably provided in the main body, and includes a transducer array configured to output an ultrasound for diagnosis of an object, the main body including: a transceiver configured to transmit and receive a signal to and from the transducer array through a plurality of channels; and at least one processor configured to control the transceiver to transmit a predetermined test signal to the
(Continued)

transducer array of the head mounted to the main body, determine a probe type corresponding to the transducer array of the mounted head based on a feedback signal received through the transceiver in response to the test signal, and make the probe apparatus operate corresponding to the determined probe type.

18 Claims, 27 Drawing Sheets

(52) U.S. Cl.
CPC .......... *A61B 8/4455* (2013.01); *A61B 8/4488* (2013.01); *A61B 8/54* (2013.01); *A61B 8/58* (2013.01); *G01S 7/5208* (2013.01); *G01S 7/52082* (2013.01); *A61B 8/4427* (2013.01); *A61B 8/4483* (2013.01); *A61B 8/461* (2013.01); *A61B 8/467* (2013.01); *A61B 8/565* (2013.01); *A61B 8/585* (2013.01); *G01S 7/5205* (2013.01)

(56) References Cited

U.S. PATENT DOCUMENTS

| | | |
|---|---|---|
| 2004/0211240 A1 | 10/2004 | Gessert et al. |
| 2013/0253327 A1 | 9/2013 | Ko et al. |
| 2014/0171802 A1 | 6/2014 | Kuroiwa et al. |
| 2014/0320153 A1* | 10/2014 | Johnson ............. G01R 1/06788 324/713 |
| 2015/0032004 A1 | 1/2015 | Kim et al. |
| 2015/0235553 A1 | 8/2015 | Broszeit |
| 2015/0236236 A1* | 8/2015 | Lewis ...................... A61N 7/00 601/2 |

FOREIGN PATENT DOCUMENTS

| | | |
|---|---|---|
| JP | 2006-095288 | 4/2006 |
| JP | 2006-095291 | 4/2006 |
| JP | 2009-279023 | 12/2009 |
| JP | 2013-056188 | 3/2013 |
| KR | 10-2007-0002131 | 1/2007 |
| KR | 10-2010-0118157 | 11/2010 |
| KR | 10-2015-0012144 | 2/2015 |

OTHER PUBLICATIONS

Extended Search Report dated Sep. 19, 2018 in counterpart EP Application No. 16855779.1.
English-language machine translation of JPH09-292377.
Communication under Rule 71(3) EPC dated May 19, 2021 in counterpart European Patent Application No. 16855779.1.
Svilainis, L. et al. "Evaluation of the ultrasonic transducer electrical matching performance," ISSN 1392-2114 Ultrasound, vol. 62, No. 4, 2007, XP055801669, 7 pages.

* cited by examiner

FIG. 1
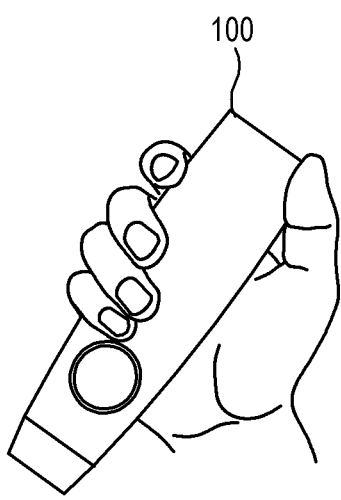
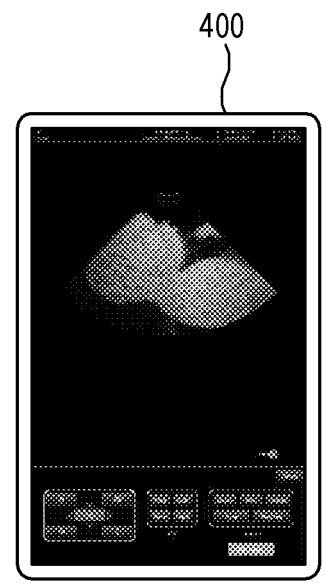

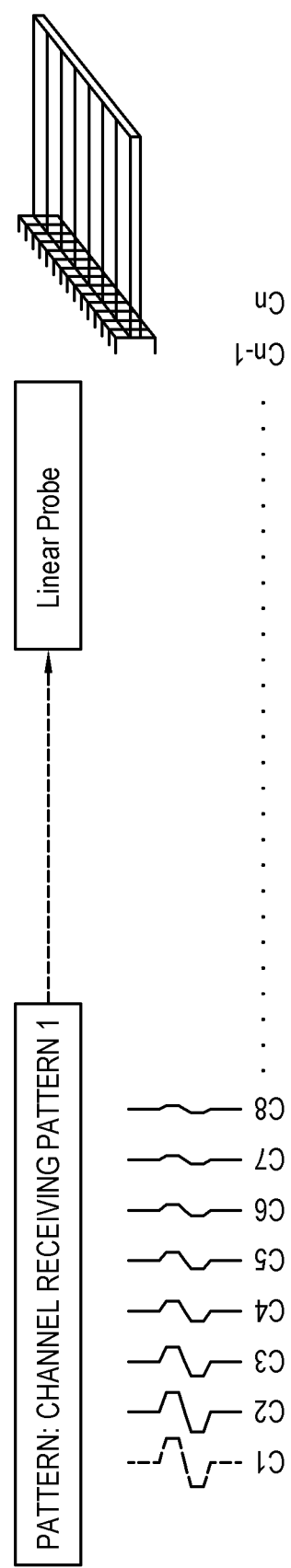

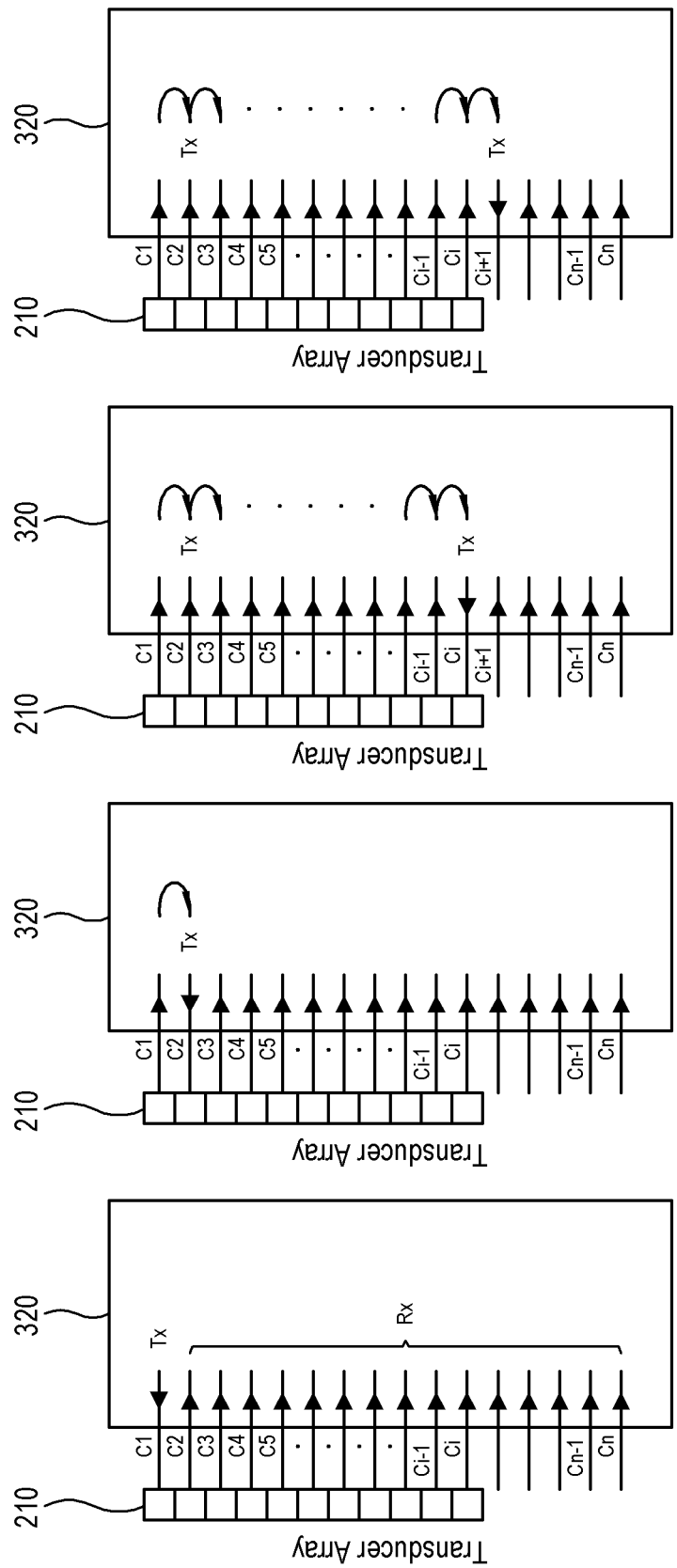

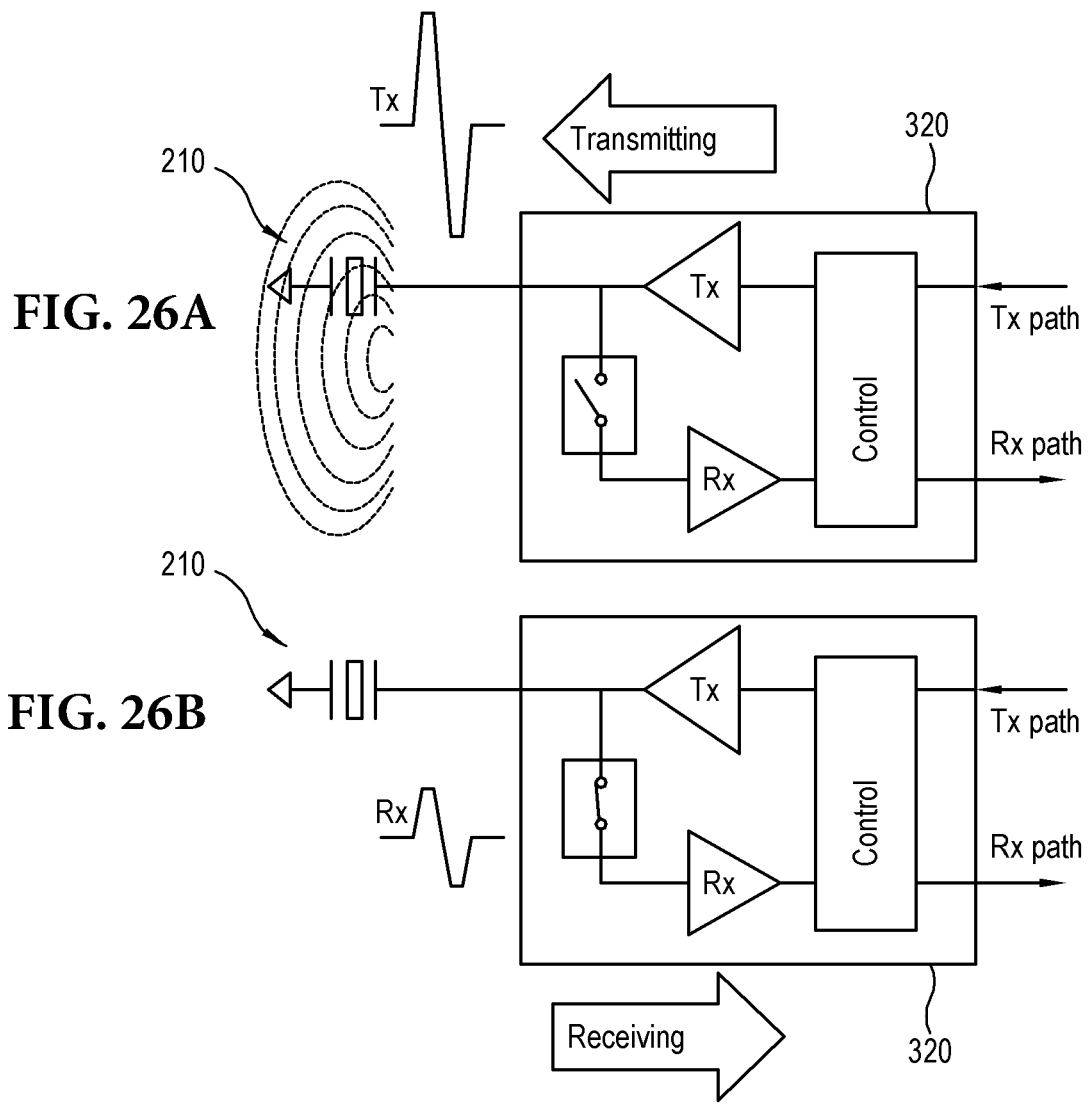

PROBE APPARATUS, MEDICAL INSTRUMENT COMPRISING SAME, AND CONTROL METHOD OF PROBE APPARATUS

This application is the U.S. national phase of International Application No. PCT/KR2016/011570 filed Oct. 14, 2016 which designated the U.S. and claims priority to KR Patent Application No. 10-2015-0144749 filed Oct. 16, 2015, the entire contents of each of which are hereby incorporated by reference.

TECHNICAL FIELD

The present disclosure relates to a probe apparatus including a transducer array, a medical instrument including the same, and a method of controlling the probe apparatus.

BACKGROUND ART

With development of electronic technology, various types of electronic products have been developed and propagated. In particular, various display apparatuses such as a smart phone, a smart pad (e.g. a tablet computer), a smart TV, a desktop computer, a laptop computer, a personal digital assistant (PDA), and the like have been frequently used even in a private home. Such development of the electronic technology is also applicable to a medical field and a health care field, and its influence has gradually expanded.

For example, an ultrasound examination may be performed in the medical field and the health care field, in which a probe apparatus to be in close-contact with a body of a patient and obtain an ultrasound image by transceiving an ultrasound is mostly employed at such an ultrasound examination.

The probe apparatus transmits an ultrasound signal to an object and receives the ultrasound signal reflected from the object, thereby providing a two- or three-dimensional ultrasound image of an interesting entity inside the object to a user through a display apparatus.

Further, the probe apparatus is portable and usable in an accident scene or inside an ambulance regardless of place, and variously utilized in visit treatment, telemedicine, etc. as it comes into use for a household or personal apparatus in the future.

The probe apparatus is internally provided with a transducer that interconverts an ultrasound signal and an electric signal, in which the transducer has various array structures in accordance with patterns where a plurality of elements is arrayed.

The probe apparatus employs a transducer having an array structure adapted for measurement and diagnosis purposes, and thus operations have to be implemented corresponding to the used transducer array.

SUMMARY

According to one embodiment of the present disclosure, a medical probe apparatus includes: a main body; a head which is detachably provided in the main body, and includes a transducer array configured to output an ultrasound for diagnosis of an object, the main body including: a transceiver configured to transmit and receive a signal to and from the transducer array through a plurality of channels; and at least one processor configured to control the transceiver to transmit a predetermined test signal to the transducer array of the head mounted to the main body, determine a probe type corresponding to the transducer array of the mounted head based on a feedback signal received through the transceiver in response to the test signal, and make the probe apparatus operate corresponding to the determined probe type. Thus, a user can selectively mount various types of transducers to an ultrasound probe in accordance with diagnosis parts and purposes.

The processor may set a parameter for making the probe apparatus operate corresponding to the determined probe type. Thus, it is possible to omit a user's manual setting procedure for using the mounted transducer.

The probe apparatus may further include a storage configured to store information corresponding to the plurality of probe types, and the processor may load information corresponding to the determined probe type from the storage and set the parameter corresponding to the loaded information. Thus, when the transducer is mounted to the probe, the parameter may be automatically set corresponding to the probe type.

The transceiver may transmit the test signal through one channel among the plurality of channels, and receive the feedback signal through channels except the channel used in transmitting the test signal among the plurality of channels. Thus, the probe type of the transducer can be sensed using the plurality of channels of the transceiver without adding other parts.

The processor may determine the probe type based on a pattern of a feedback signal received through each of the plurality of channels in sequence from a channel adjacent to the channel used in transmitting the test signal. Thus, the probe type can be easily recognized using a interference signal (or cross-talk) of the test signal.

The transducer array has a structure where the plurality of elements are arranged to have a predetermined shape, and the processor determines an element arranged shape of the transducer array based on a pattern of the feedback signal received in sequence and determines the probe type corresponding to the determined element arranged shape. Thus, an interference signal due to the element arranged shape of the transducer array may be used in determining the probe type.

The element arranged shape of the transducer array corresponding to the probe type may include at least one of linear, convex and phased types. Thus, the transducer having various element arranged shapes may be selectively mounted to the probe.

The processor may control the transceiver to transmit the test signal to the transducer array through each of the plurality of channels, and initialize the transceiver by correcting an error between the plurality of channels based on deviation of the feedback signals received according to the plurality of channels of transmitting the test signal. Thus, the test signal can be utilized in correcting the deviation between the channels of the transceiver, thereby preventing an error from occurring in the signal transceiving procedure.

The processor may determine whether a channel of transmitting the test signal among the plurality of channels and the transducer array are connected or not based on the feedback signal, and cut off power supplied to at least one among the plurality of channels based on a result of the determination. Thus, connection with the array elements is grasped according to channels without adding parts or control procedure, thereby having effects on reducing wasteful power consumption.

The processor may determine whether the transducer array and the channel used in transmitting the test signal are connected or not, based on the feedback signal responding to the test signal transmitted through at least some of the plurality of channels. Thus, the test signals from not the whole channels but some channels are used to thereby conveniently grasp connection with or disconnection from the array element.

The processor may use the feedback signal received through at least some among the plurality of channels in response to the test signal, thereby determining whether the channel used in transmitting the test signal and the transducer array are connected or not. Thus, the connection or disconnection is grasped without using the feedback signals of the whole channels, thereby having an effect on simplifying an operation process.

The plurality of channels may correspond to arranged elements of the transducer array, and the number of elements in the transducer array may be lower than or equal to the number of channels. Thus, various transducers different in the number of elements are selectively mountable to the probe apparatus.

The processor may control the transceiver to transmit the test signal to the transducer array through each of the plurality of channels, and detect whether the element of the transducer array connected to each of the plurality of channels is damaged or not, based on feedback signals received through the plurality of channels used in the test signal. Thus, the test signal is utilized in detecting whether the element is damaged or not.

The probe apparatus may further include a communicator communicable with the display apparatus of displaying an image, and the processor may control the communicator to send the display apparatus a message of notifying a user of information about the probe apparatus corresponding to a determination result through the probe apparatus. Thus, a user can be informed of various pieces of information including the probe type, thereby improving user convenience.

The processor may detect a level of the feedback signal, determines impedance of the transducer array based on the detected signal level, and adjust a level of power supplied to the transducer array to correspond to the determined impedance. Thus, the feedback signal is utilized to prevent the transducer from being supplied with excessively high or low power, thereby optimizing an operation of an element and a power efficiency.

The transceiver may be provided with a switch for connecting an internal path, and the processor may control the transceiver to pass a second test signal therethrough with regard to each of the plurality of channels while the switch is turned on, and initialize the transceiver by correcting an error between the plurality of channels based on deviation of second test signals passed through the transceiver. Thus, it is possible to correct an error that may occur in the transceiver during a manufacturing procedure.

By the way, according to one embodiment of the present disclosure, a medical instrument includes a probe apparatus and a display apparatus, the probe apparatus including: a main body, and a head which is detachably provided in the main body, and includes a transducer array configured to output an ultrasound for diagnosis of an object, the main body including: a transceiver configured to transmit and receive a signal to and from the transducer array through a plurality of channels; at least one processor configured to control the transceiver to transmit a predetermined test signal to the transducer array of the head mounted to the main body, determine a probe type corresponding to the transducer array of the mounted head based on a feedback signal received through the transceiver in response to the test signal, and make the probe apparatus operate corresponding to the determined probe type; and a communicator configured to communicate with the display apparatus and transmit information about an ultrasound signal reflected from the object to the display apparatus, and the display apparatus displaying an ultrasound image generated based on information received through the communicator. Thus, a user can selectively mount various types of transducers to an ultrasound probe in accordance with diagnosis parts and purposes.

The processor may set a parameter for making the probe apparatus operate corresponding to the determined probe type. Thus, it is possible to omit a user's manual setting procedure for using the mounted transducer.

The medical instrument may further include a storage configured to store information corresponding to the plurality of probe types, and the processor may load information corresponding to the determined probe type from the storage and set the parameter corresponding to the loaded information. Thus, when the transducer is mounted to the probe, the parameter may be automatically set corresponding to the probe type.

The transceiver may transmit the test signal through one channel among the plurality of channels, and receive the feedback signal through channels except the channel used in transmitting the test signal among the plurality of channels. Thus, the probe type of the transducer can be sensed using the plurality of channels of the transceiver without adding other parts.

The processor may determine the probe type based on a pattern of a feedback signal received through each of the plurality of channels in sequence from a channel adjacent to the channel used in transmitting the test signal. Thus, the probe type can be easily recognized using an interference signal of the test signal.

The transducer array has a structure where the plurality of elements are arranged to have a predetermined shape, and the processor determines an element arranged shape of the transducer array based on a pattern of the feedback signal received in sequence and determines the probe type corresponding to the determined element arranged shape. Thus, an interference signal due to the element arranged shape of the transducer array may be used in determining the probe type.

The element arranged shape of the transducer array corresponding to the probe type may include at least one of linear, convex and phased types. Thus, the transducer having various element arranged shapes may be selectively mounted to the probe.

The processor may control the transceiver to transmit the test signal to the transducer array through each of the plurality of channels, and initialize the transceiver by correcting an error between the plurality of channels based on deviation of the feedback signals received according to the plurality of channels of transmitting the test signal. Thus, the test signal can be utilized in correcting the deviation between the channels of the transceiver, thereby preventing an error from occurring in the signal transceiving procedure.

The processor may determine whether a channel of transmitting the test signal among the plurality of channels and the transducer array are connected or not based on the feedback signal, and cut off power supplied to at least one among the plurality of channels based on a result of the determination. Thus, connection with the array elements is grasped according to channels without adding parts or control procedure, thereby having effects on reducing wasteful power consumption.

The processor may determine whether the transducer array and the channel used in transmitting the test signal are connected or not, based on the feedback signal responding to the test signal transmitted through at least some of the plurality of channels. Thus, the test signals from not the whole channels but some channels are used to thereby conveniently grasp connection with or disconnection from the array element.

The processor may use the feedback signal received through at least some among the plurality of channels in response to the test signal, thereby determining whether the channel used in transmitting the test signal and the transducer array are connected or not. Thus, the connection or disconnection is grasped without using the feedback signals of the whole channels, thereby having an effect on simplifying an operation process.

The plurality of channels may correspond to arranged elements of the transducer array, and the number of elements in the transducer array may be lower than or equal to the number of channels. Thus, various transducers different in the number of elements are selectively mountable to the probe apparatus.

The processor may control the transceiver to transmit the test signal to the transducer array through each of the plurality of channels, and detect whether the element of the transducer array connected to each of the plurality of channels is damaged or not, based on feedback signals received through the plurality of channels used in the test signal. Thus, the test signal is utilized in detecting whether the element is damaged or not.

The medical instrument may further include a display on which a message including information about the probe apparatus corresponding to the determination results of the probe type is displayed. Thus, a user can be informed of various pieces of information including the probe type, thereby improving user convenience.

The processor may detect a level of the feedback signal, determines impedance of the transducer array based on the detected signal level, and adjust a level of power supplied to the transducer array to correspond to the determined impedance. Thus, the feedback signal is utilized to prevent the transducer from being supplied with excessively high or low power, thereby optimizing an operation of an element and a power efficiency.

The transceiver may be provided with a switch for connecting an internal path, and the processor may control the transceiver to pass a second test signal therethrough with regard to each of the plurality of channels while the switch is turned on, and initialize the transceiver by correcting an error between the plurality of channels based on deviation of second test signals passed through the transceiver. Thus, it is possible to correct an error that may occur in the transceiver during a manufacturing procedure.

The display apparatus may include at least one of a smart phone, a tablet computer, a notebook computer, a monitor, and a television. Thus, the portable probe apparatus can be used interworking with various display apparatuses.

By the way, according to one embodiment of the present disclosure, a method of controlling a probe apparatus including a main body and a head detachably provided in the main body includes: sensing whether a head including a transducer array configured to output an ultrasound for diagnosis of an object is mounted to the main body; transmitting a predetermined test signal to the transducer array; determining a probe type corresponding to the transducer array of the mounted head based on a feedback signal received in response to the test signal; and making the probe apparatus operate corresponding to the determined probe type. Thus, a user can selectively mount various types of transducers to an ultrasound probe in accordance with diagnosis parts and purposes.

The method may further include: setting a parameter for making the probe apparatus operate corresponding to the determined probe type. Thus, it is possible to omit a user's manual setting procedure for using the mounted transducer.

The method may further include loading information about the determined probe type from the storage, and the setting of the parameter may include setting the parameter to correspond to the loaded information. Thus, when the transducer is mounted to the probe, the parameter may be automatically set corresponding to the probe type.

The transmitting of the test signal may include: transmitting the test signal through one channel among the plurality of channels of the transceiver provided in the probe apparatus; and receiving the feedback signal through channels except the channel used in transmitting the test signal among the plurality of channels. Thus, the probe type of the transducer can be sensed using the plurality of channels of the transceiver without adding other parts.

The determining of the probe type may include: determining the probe type based on a pattern of a feedback signal received through each of the plurality of channels in sequence from a channel adjacent to the channel used in transmitting the test signal. Thus, an interference signal cause by the element arranged shape of the transducer array may be used in determining the probe type.

The transducer array may have a structure where the plurality of elements are arranged to have a predetermined shape, and the determining of the probe type may include determining an element arranged shape of the transducer array based on a pattern of the feedback signal received in sequence and determining the probe type corresponding to the determined element arranged shape. Thus, an interference signal due to the element arranged shape of the transducer array may be used in determining the probe type.

The element arranged shape of the transducer array corresponding to the probe type may include at least one of linear, convex and phased types. Thus, the transducer having various element arranged shapes may be selectively mounted to the probe.

The transmitting of the test signal may include transmitting the test signal to the transducer array through each of the plurality of channels of the transceiver provided in the probe apparatus, and the determining of the probe type may include correcting an error between the plurality of channels based on deviation of the feedback signals received according to the plurality of channels of transmitting the test signal. Thus, the test signal can be utilized in correcting the deviation between the channels of the transceiver, thereby preventing an error form occurring in the signal transceiving procedure.

The determining of the probe type may include: determining whether a channel of transmitting the test signal among the plurality of channels of the transceiver provided in the probe apparatus and the transducer array are connected or not based on the feedback signal; and cutting off power supplied to at least one among the plurality of channels based on a result of the determination. Thus, connection with the array elements is grasped according to channels without adding parts or control procedure, thereby having effects on reducing wasteful power consumption.

The determining of the connection or disconnection may include determining whether the transducer array and the channel used in transmitting the test signal are connected or not, based on the feedback signal responding to the test signal transmitted through at least some of the plurality of channels. Thus, the test signals from not the whole channels but some channels are used to thereby conveniently grasp connection with or disconnection from the array element.

The determining of the connection or disconnection may include using the feedback signal received through at least some among the plurality of channels in response to the test signal, thereby determining whether the channel used in transmitting the test signal and the transducer array are connected or not. Thus, the connection or disconnection is grasped without using the feedback signals of the whole channels, thereby having an effect on simplifying an operation process.

The plurality of channels of the transceiver provided in the probe apparatus may correspond to arranged elements of the transducer array, and the number of elements in the transducer array may be lower than or equal to the number of channels. Thus, various transducers different in the number of elements are selectively mountable to the probe apparatus.

The transmitting of the test signal may include transmitting the test signal to the transducer array through each of the plurality of channels of the transceiver provided in the probe apparatus, and detecting whether the element of the transducer array connected to each of the plurality of channels is damaged or not, based on feedback signals received through the plurality of channels used in the test signal. Thus, the test signal is utilized in detecting whether the element is damaged or not.

The method may further include displaying a message of showing the determined probe type. Thus, a user can be informed of various pieces of information including the probe type, thereby improving user convenience.

The determining of the probe type may include detecting a level of the feedback signal; determining impedance of the transducer array based on the detected signal level; and adjusting a level of power supplied to the transducer array to correspond to the determined impedance. Thus, the feedback signal is utilized to prevent the transducer from being supplied with excessively high or low power, thereby optimizing an operation of an element and a power efficiency.

According to one embodiment of the present disclosure, there is provided an ultrasound probe apparatus which can automatically recognize a probe type and operate according to the recognized probe types. Therefore, the head of various types is connected to the main body in accordance with diagnosis purposes.

Further, the parameter is automatically set in accordance with the determined probe types, and thus a user does not have to manually input setting values, thereby more improving user convenience.

Further, the test signal is transmitted using the plurality of channels of the transceiver, and the feedback signal received in response to the test signal is used in recognizing the probe type, thereby automatically optimizing an operation to the mounted probe type without additional parts or costs.

Further, the test signal may be variously utilized in measuring the impedance of the transducer array, recognizing the number of array elements, determining about whether the transducer is damaged, characteristic compensation according to the channels of the transceiver, etc.

BRIEF DESCRIPTION OF THE DRAWINGS

FIG. 1 is a view of illustrating a medical instrument according to one embodiment of the present disclosure, FIGS. 13, 14A, 14B, 15, 16, 17, 18, and 19 are views for illustrating a procedure of determining a probe type of a transducer array in the probe apparatus according to one embodiment of the present disclosure, FIGS. 20A, 20B, 20C, 20D, 21A, 21B, and 22 are views for illustrating a procedure of correcting an error between channels in the probe apparatus according to one embodiment of the present disclosure, FIGS. 25A, 25B, 26A, and 26B are views for illustrating a procedure of adjusting a power level based on impedance of the transducer array in the probe apparatus according to one embodiment of the present disclosure.

Figure 2:
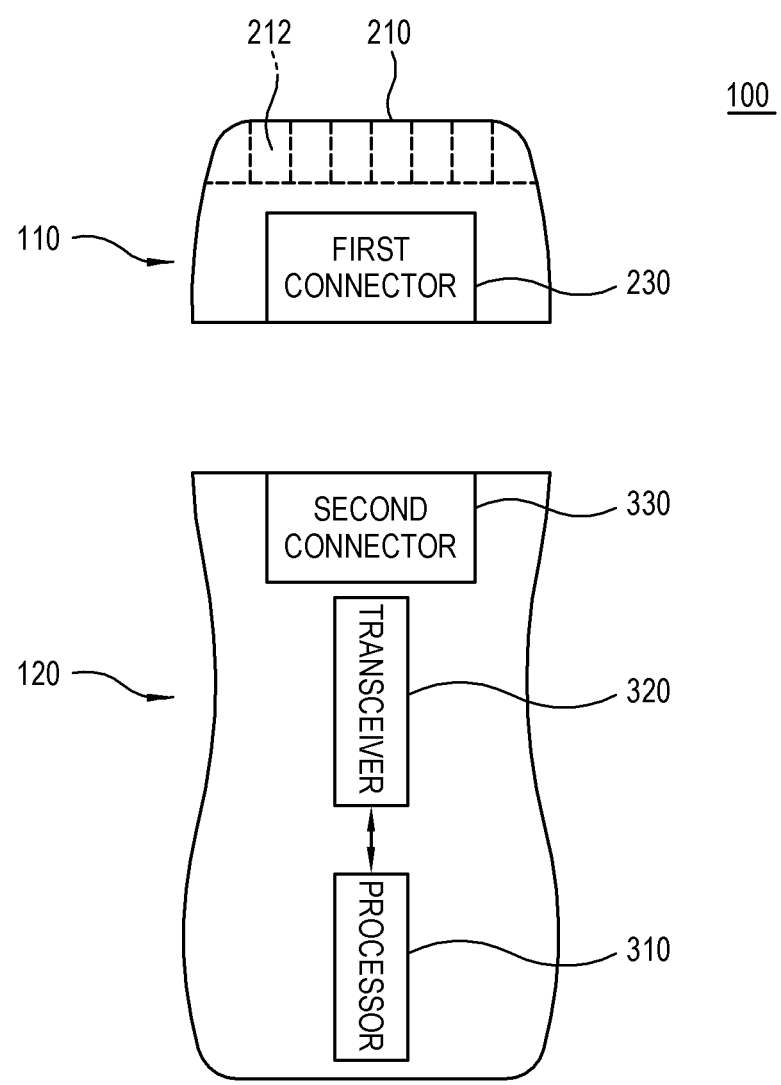
FIG. 2 is a view of schematically illustrating a probe apparatus according to one embodiment of the present disclosure.

| * Description of reference numerals* | |
|---|---|
| 100: probe apparatus | 110, 111, 112, 113: head |
| 120: main body | 210: transducer |
| 310: processor | 320: transceiver |
| 340: storage | 350: first communicator |
| 400: display apparatus | 10: medical instrument |

DETAILED DESCRIPTION OF EXAMPLE EMBODIMENTS

Below, exemplary embodiments will be described with reference to accompanying drawings to such an extent as to be easily realized by a person having an ordinary knowledge in the art. The present inventive concept is not limited to the embodiments set forth herein, and may be materialized variously.

Terms to be used in the following descriptions will be selected as general terms currently used as widely as possible taking functions of elements into account, but may be varied depending on intent of those skilled in the art, precedents, the advent of new technology, etc. In particular, there may be a term voluntarily selected by the applicant. In this case, the meaning of the term will be explained in detail through the relevant detailed descriptions. Therefore, the terms set forth herein have to be read in light of its meaning and content throughout the following descriptions rather than naming.

In the following descriptions, terms such as "include" or "have" refer to presence of features, numbers, steps, operations, elements or combination thereof, and do not exclude presence or addition of one or more other features, numbers, steps, operations, elements or combination thereof.

A "portion" set forth herein refers to software or hardware such as FPGA or ASIC, and performs certain roles. However, the meaning of the "portion" is not limited to software or hardware. The "portion" may be configured to be present in a storage medium for addressing or may be configured to reproduce one or more processors. For example, the "portion" includes software elements, object-oriented software elements, class elements, task elements and the like elements, and processes, functions, attributes, procedures, subroutines, segments of a program code, drivers, firmware, a microcode, a circuit, data, a database, data structures, tables, arrays and variables. The function provided in the elements and the "portions" may be carried out by combining fewer elements and "portions" or may be subdivided by additional elements and "portions".

For clarity, elements not directly related to the elements of the exemplary embodiment may be omitted, and like numerals refer to like elements throughout.

In this specification, an image may indicate multi-dimensional data configured with discrete image elements (for example, pixels in a two-dimensional (2D) image and voxels in a three-dimensional (3D) image). For example, the image may include a medical image and the like of an object, obtained by an ultrasound signal.

Further, in this specification, an "object" may include a human or an animal, or a part of the human or animal. For example, the object may include a liver, a heart, a uterus, a brain, a breast, an abdomen and the like organs, or a blood vessel. Further, the "object" may include a phantom. The phantom refers to a material having a volume, which is very approximate to the density and the effective atomic number of living things, and may include a sphere phantom having similar properties to a human body.

Further, in this specification, a "user" refers to a medical expert such as a doctor, a nurse, a medical laboratory technologist, a medical image specialist, etc. or a technician of repairing a medical device, but is not limited thereto.

For clarity of the present disclosure in association with the drawings, portions not directly related to the elements of the present disclosure may be omitted, and like numerals refer to like elements throughout.

FIG. 1 is a view of illustrating a medical instrument according to one embodiment of the present disclosure.

As an ultrasonography machine, the medical instrument 10 according to one embodiment of the present disclosure shown in FIG. 1 means at least one device that transmits an ultrasound signal from the surface of the object body toward a predetermined part in the inside of the body, and obtains an image of a blood flow or plane section of soft tissue based on information of an ultrasound signal (hereinafter, referred to as an ultrasound eco signal) reflected from the tissue inside the body.

According to one embodiment of the present disclosure, the medical instrument 10 may be provided as a system including a plurality of apparatuses that obtains an ultrasound medical image, and displays the obtained medical image on a screen.

Specifically, as shown in FIG. 1, the medical instrument 10 includes a probe apparatus 100 (hereinafter, referred to as a 'probe') that outputs an ultrasound signal to an object and receives an ultrasound signal, i.e. an ultrasound echo signal reflected from the object in response to the output ultrasound signal, and a display apparatus 300 that displays an ultrasound image based on the ultrasound echo signal received from the probe apparatus 100.

According to one embodiment of the present disclosure, the medical instrument 10 may be materialized in various forms. For example, in this specification, the probe apparatus 100 to be described in this specification may be achieved in the form of a mobile terminal as well as a stationary terminal. When the probe apparatus 100 is materialized by the mobile terminal, there are a smart phone, a smart pad such as a tablet computer, a smart TV, a desktop computer, a laptop computer, a personal digital assistant (PDA), and the like as examples of the display apparatus 300. FIG. 1 illustrates an example of when the display apparatus 300 is the tablet computer.

According to one embodiment of the present disclosure, the medical instrument 100 may exchange medical image data with other medical devices in hospital or hospital servers connected through a picture archiving and communication system (PACS). Further, the medical instrument 100 may perform data communication with a server or the like in accordance with standards of digital imaging and communications in medicine (DICOM).

According to one embodiment of the present disclosure, the display apparatus 300 involved in the medical instrument 10 may include the touch screen. The touch screen may be configured to detect not only a touch input position and a touched area, but also a touch input pressure. Further, the touch screen may be configured to detect a proximity touch as well as a real touch.

In this specification, the real touch refers to an input caused by real contact between a screen and a user's body (e.g. a finger) or a touch pen given as a touch tool (e.g. a pointing device, a stylus, a haptic pen, an electronic pen, etc.). The proximity touch refers to an input caused by not real contact between a screen and a user's body or a touch tool but an approach up to a predetermined distance from the screen (e.g. hovering within a detectable distance of 30 mm or less).

The touch screen may be for example achieved by a resistive type, a capacitive type, an infrared type, or an acoustic wave type.

According to one embodiment of the present disclosure, the display apparatus 300 involved in the medical instrument 10 may sense a gesture input as a user's touch input to a medical image through the touch screen.

As a user's touch input to be described in this specification, there are a tap, a click stronger than the tap, touch and hold, a double tap, a double click, a drag corresponding to movement by a predetermined distance while keeping the touch, drag and drop, slide, flicking, panning, swipe, pinch, etc. The drag, slide, flicking, swipe, and the like input is divided into press corresponding to contact between the touch screen and a finger (or a touch pen), movement by a predetermined distance, and release from the touch screen, and includes all kinds of movement in the form of a straight line or a curved line. These various touch inputs are involved in the gesture input.

According to one embodiment of the present disclosure, the medical instrument 10 may provide some or all of buttons for controlling a medical image in the form of a graphic user interface (GUI) through the display apparatus 300.

According to one embodiment, the medical instrument 10 employs the probe apparatus 100 to emit an ultrasound signal to an interesting region of an object, and detect a reflected ultrasound signal, i.e. an ultrasound echo signal, thereby generating an ultrasound image to be displayed on the display apparatus 300.

The probe apparatus 100 is generally connected to a main body of an ultrasound diagnosis device and serves for transceiving an ultrasound signal with regard to an object while being in contact with an examination portion of the object. According to one embodiment of the present disclosure, the probe apparatus 100 may serve only for transceiving an ultrasound signal with regard to an object, or may serve for generating an image based on a received ultrasound signal as well as transceiving the ultrasound signal. That is, when the existing ultrasound examination system is divided into a main body of an ultrasound diagnosis device and a probe, the probe apparatus 100 according to one embodiment of the present disclosure is defined to include only the probe, or both the main body of the ultrasound diagnosis device and the probe.

FIG. 2 is a view of schematically illustrating the probe apparatus 100 according to one embodiment of the present disclosure.

Referring to FIG. 2, the probe apparatus 100 includes a head 110 (hereinafter, referred to as a 'probe head') which transmits ultrasound for a diagnosis of an object and receives an echo, and a main body 120 (hereinafter, referred to as a 'probe main body') to which the head 110 is mounted.

As shown in FIGS. 1 and 2, the probe apparatus 100 according to one embodiment of the present disclosure is portable to be carried or moved as it is gripped by a user.

The head 110 is a portion to be in contact with an object, and includes a transducer 210 for emitting ultrasound to an object and receiving an echo signal of an ultrasound reflected from the object. In this embodiment, the transducer 210 refers to a transducer array in which a plurality of elements (hereinafter, referred to as 'transducer elements') 212 for interconverting an electric signal and an audio signal is arrayed in a predetermined form.

As the transducer 210, for example, there may be used various kinds of ultrasound transducer such as a piezoelectric ultrasonic transducer using a piezoelectric effect of a piezoelectric material, a capacitive micromachined ultrasonic transducer (cMUT) for interconverting ultrasound and electric signals based on capacitive changes, a magnetic micromachined ultrasonic transducer (mMUT) for interconverting ultrasound and electric signals based on magnetic changes, an optical ultrasonic detector for interconverting ultrasound and electric signals based on optical changes, etc.

The plurality of elements 212 may include a plurality of piezoelectric elements. The plurality of piezoelectric elements may be formed by dividing the piezoelectric material into a plurality of pieces. For example, the plurality of piezoelectric elements may be formed by dicing an elongated piezoelectric material. However, there are no limits to the method of dividing and manufacturing the plurality of piezoelectric elements. For example, the plurality of piezoelectric elements may be formed by pressing the piezoelectric material against a metal mold, or by other various methods. The piezoelectric material may include piezoelectric ceramics, single crystal, a composite piezoelectric material made up of these materials and polymer, and the like causing a piezoelectric phenomenon.

The transducer array 210 includes the piezoelectric element as the element for interconverting the ultrasound and electric signals, but is not limited thereto. That is, various ultrasound transducers described above may be usable, and the plurality of elements may be variously achieved corresponding to the kinds of ultrasound transducer.

The plurality of elements 212 may be arranged in ways of a linear array and a curved (i.e. convex) array. Further, the plurality of elements 212 may be arranged in a plurality of layers, that is, a double- or multi-layered array (i.e. a phased array). The array type may be varied depending on intention of a designer. Such arranged elements may be provided with a cover for covering the plurality of elements 121.

When the transducer 210 includes the plurality of elements arranged one-dimensionally on a plane perpendicular to a traveling direction of ultrasound, it is referred to as a one-dimensional transducer array. The one-dimensional transducer array may be the linear array, but may also be the convex array. The one-dimensional transducer array has advantages of low costs since it is easily manufactured.

Further, the plurality of elements 212 of the transducer 210 may be two-dimensionally arranged on a plane perpendicular to the traveling direction of the ultrasound, and this is referred to as a two-dimensional transducer array. The two-dimensional transducer array may be the linear array, but may also be the curved array.

Here, the two-dimensional transducer array properly delays an input time of signals input to each individual element, and transmits the delayed signals to an object along an external scan line for transmitting the ultrasound. Further, a plurality of echo signals is employed to obtain a stereoscopic image. Therefore, the two-dimensional transducer array may be more useful to achieve a 3D image.

The probe apparatus 100 may further include a light source (not shown). The light source is to emit light to the inside of the object. For example, at least one light source for emitting light having a specific wavelength may be used as the light source. Alternatively, a plurality of light sources for emitting light having different wavelengths may be used as the light source. The wavelength of the light emitted from the light source may be selected in consideration of a target inside the object. Such a light source may be materialized by a semiconductor laser (LD), a light emitting diode (LED), a solid laser, a gas laser, an optical fiber, or combination thereof.

When ultrasound having several to hundreds of MHz is applied from the probe apparatus 100 to a specific part of a patient's body, this ultrasound is partially reflected from layers between many other tissues. The ultrasound is reflected from anatomical entities, which is change in density in the body, for example, blood cells in blood plasma, small structures in organs, etc.

The transducer array 210 provided in the probe apparatus 100 generates an ultrasound signal in response to a control signal, and emits the generated ultrasound signal to the object. Then, the ultrasound echo signal reflected from a specific organ (e.g. lesion) inside the object is received, i.e. detected.

The reflected ultrasound vibrates the transducer 210 of the probe apparatus 100, and the transducer 210 outputs electrical pulses corresponding to the vibration. The electric pulses are converted into an image and displayed through the display apparatus 300. When the anatomical entities are different in properties of reflecting the ultrasound, for example, in an ultrasound image of a brightness (B) mode, the anatomical entities are displayed to be different in brightness.

As shown in FIG. 2, the probe head 110 is detachably provided in the main body 120. The main body 120 internally includes at least one processor 310 for controlling the transducer array 210 of the head 110 to emit and receive the ultrasound signal, and a transceiver 320 for transceiving a signal with regard to the transducer array 210 through a plurality of channels.

Electric connection or disconnection between the transducer 210 and the processor 310 may be performed by coupling or separation between the head 110 and the main body 120. The coupling between the head 110 and the main body 120 may be for example performed by inserting a portion of the head 110 into the main body 120. Here, the portion of the head 110 to be inserted in the main body 120 may correspond to a region excluding a region where the transducer 210 is arranged. For example, the portion of the head 110 may correspond to a region of the probe head 110, which is opposite to a region where the transducer array 210 is arranged.

For electric connection between the probe head 110 and the probe main body 120, the head 110 and the main body 120 may respectively include a first connector 230 and a second connector 330.

The first connector 230 provided in the head 110 is used in transmitting an electric signal from the transducer 210 to the transceiver 320 of the main body 120. The first connector 230 may be partially exposed while being arranged in the region opposite to the region, in which the transducer 210 is arranged, in the probe head 110. Therefore, when the head 110 is coupled to the main body 120, the first connector 230 is in contact with the second connector 330 of the main body 120. Hereinafter, the region where the transducer 210 is arranged will be called a front end of the probe head 110, and the region where the first connector 230 of the probe head 110 is exposed will be called a back end of the probe head 110.

Further, the second connector 330 provided in the main body 120 is used in transmitting a signal from the transducer array 210 of the head 110 to the transceiver 320. The second connector 330 may be arranged in a front end of the main body 120 and partially exposed. Therefore, when the main body 120 is coupled to the head 110, the second connector 330 is in contact with the first connector 230 of the head 110. The first connector 230 and the second connector 330 may include a conductive material capable of transmitting a signal.

Figure 3:
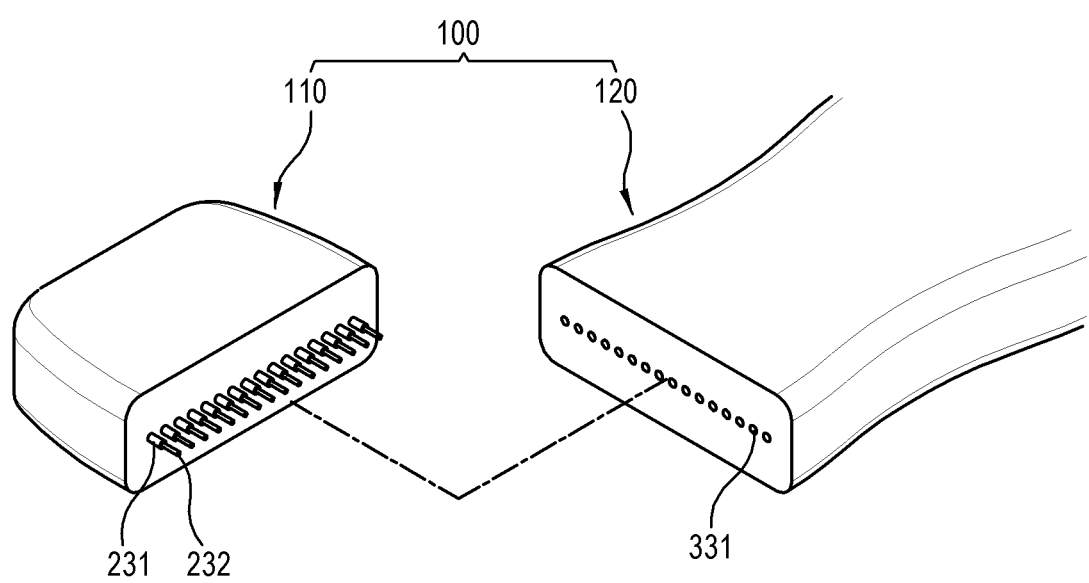
FIGS. 3 and 4 are views of illustrating examples of connection between a head and a main body according to one embodiment of the present disclosure.
Figure 4:
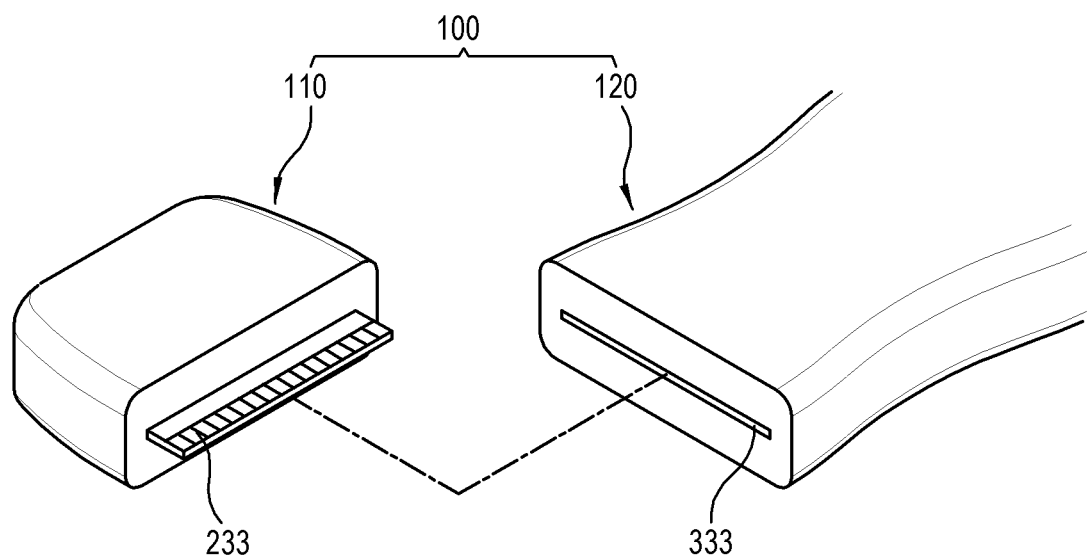

FIGS. 3 and 4 are views of schematically illustrating examples of connection between the head 110 and the main body 120 according to one embodiment of the present disclosure, In one embodiment, as shown in FIG. 3, the head 110 may include a plurality of projections 231 provided as the first connector. The plurality of projections 231 may protrude from the back end of the head 110. Further, the main body 120 may include a plurality of grooves 331 respectively corresponding to the plurality of projections 231 as the second connector. The grooves 331 may be arranged in a region corresponding to the projections 231 in the front end of the main body 120.

Here, the plurality of projections 231 may include a conductive material at the end 232 thereof, and the grooves 331 may be internally provided with a conductive material. Therefore, the plurality of projections 231 are respectively inserted in the corresponding grooves 331, and thus the first connector and the second connector are in contact with each other, thereby electrically connecting the head 110 and the main body 120.

Alternatively, as shown in FIG. 4, a first connector 233 of the head 110 is shaped like a plug, and a second connector 333 of the main body 120 may be shaped like a jack. Therefore, when the first connector 233 is connected to the second connector 333, the head 110 and the main body 120 are electrically connected to each other.

FIGS. 3 and 4 are examples of coupling the head 110 and the main body 120, and the scope of the present disclosure is not limited thereto. That is, various structures for coupling and electrically connecting the head 110 and the main body 120 with each other may be applicable to the present disclosure.

In one embodiment, the probe apparatus 100 may be provided in plural (e.g. 111, 112 and 113 of FIG. 5) having various shapes adapted for use purposes of the head 110. Thus, a user can select the head of a specific type (hereinafter, referred to as a 'probe type') having a transducer array adapted for the user purpose, for example, a head 111 (see FIG. 5) to be coupled to the main body 120.

Figure 5:
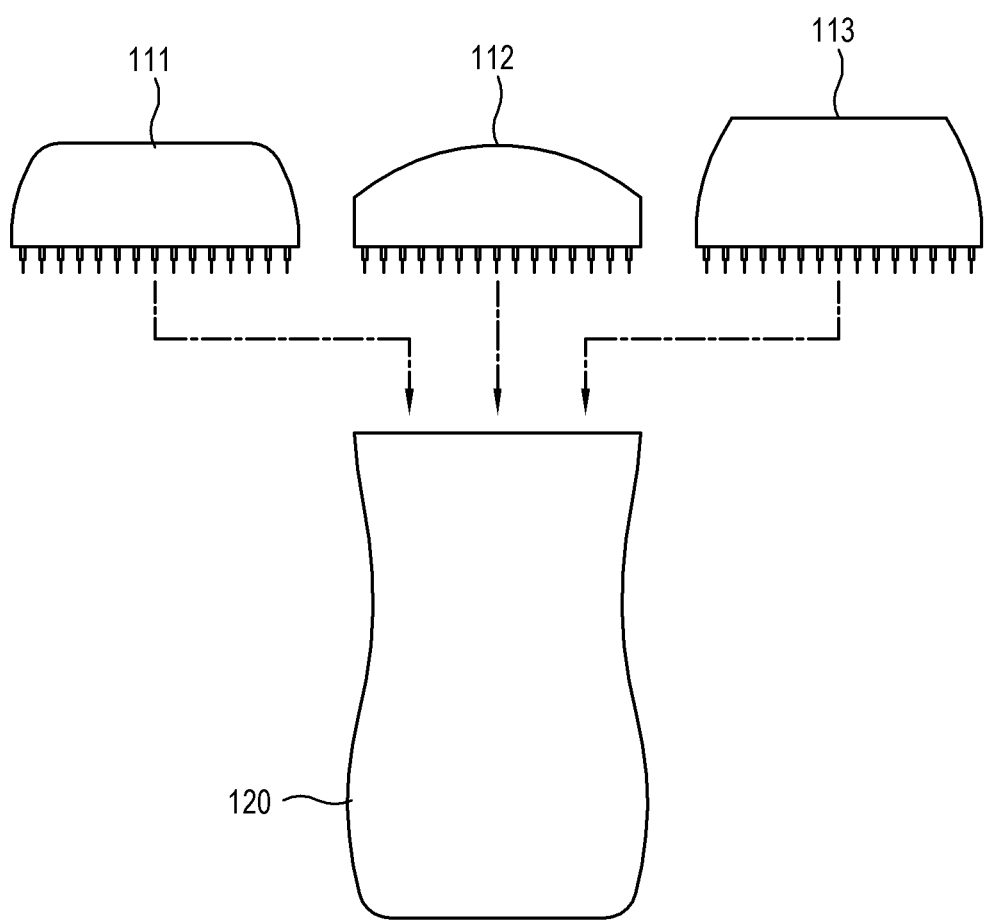
FIG. 5 is a view for schematically illustrating an example where heads are selectively connected to the main body according to one embodiment of the present disclosure.

FIG. 5 is a view for schematically illustrating an example where the head is selectively connected to the main body according to one embodiment of the present disclosure.

In one embodiment, as shown in FIG. 5, the probe apparatus 100 is provided such that the plurality of heads 111, 112 and 113 can be selectively mounted to and separated from the main body 120.

Specifically, FIG. 5 illustrates that the plurality of heads 111, 112 and 113 are respectively provided as types of a linear array 111, a convex array 112, and a phased array 113 in accordance with arranged structures of the elements of the transducer array. In the phased transducer array, the plurality of elements may be arranged in a double- or multi-layered structure.

The plurality of heads 111, 112 and 113 may for example have the coupling structure as shown in FIG. 3 or FIG. 4, and be coupled to the main body 120.

A user may select one (e.g. 111) among the plurality of heads 111, 112 and 113 in accordance with the use purposes of the probe apparatus 100, for example, body parts to be subjected to the ultrasound diagnosis, and couple the selected one to the main body 120. Then, the probe apparatus 100, of which the main body 120 couples with the head 111, is used to perform the ultrasound diagnosis.

When the use purpose is changed, a user separates the coupled head 111 from the main body 120, and couples another head 112 to the main body 120.

In this embodiment, the plurality of heads 111, 112 and 113 is selectively coupled to the main body 120 in accordance with the diagnosis purposes, and thus the probe apparatus 100 is improved in utilization.

Figure 6:
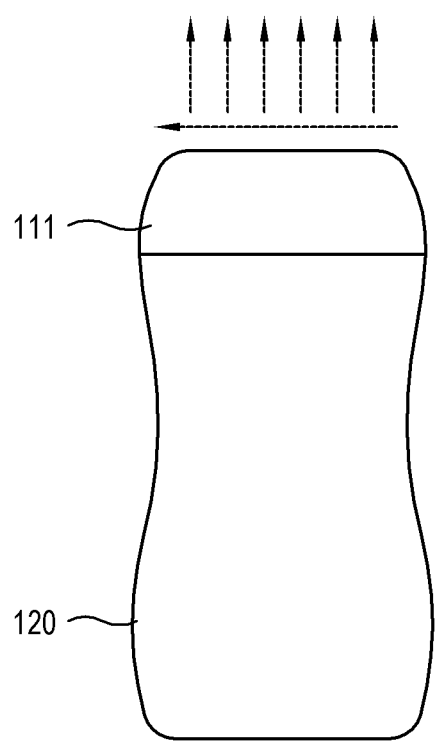
FIG. 6, FIG. 7, and FIG. 8 are views of utilizing a transducer array in accordance with the types of the head.
Figure 7:
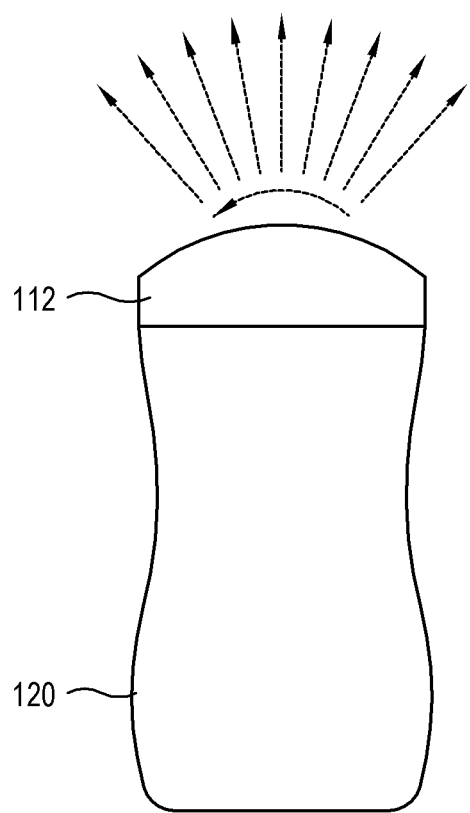
Figure 8:
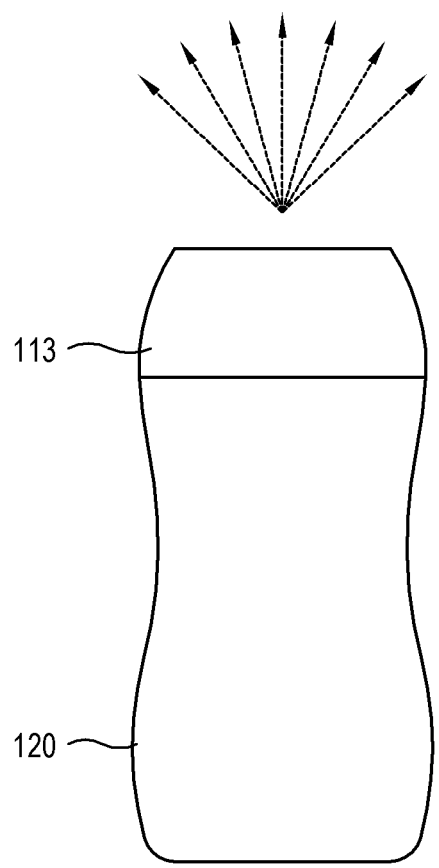

FIG. 6 to FIG. 8 are views of utilizing a transducer array in accordance with the types of the head, As shown in FIG. 6, the main body 120 may be coupled with the head 111 of the linear array type. The transducer having the head 111 of the linear array type employs a frequency of 3 to 8 MHz, and provides a diagnosis result of a body part at a shallow depth with high resolution. When the coupled head is of a linear array probe type, it may be utilizable for breast, thyroid, musculoskeletal and the like diagnoses.

In the head 111 of the linear array type according to one embodiment, diagnosis depth and use frequency may be varied depending on the standards of the transducer.

As shown in FIG. 7, the main body 120 may be coupled with the head 112 of the convex array type. The transducer having the head 112 of the linear array type employs a frequency of 2 to 5 MHz, and is provided to broadly observe a body part at a deep depth. When the coupled head is of a convex array probe type, it may be utilized for abdominal diagnoses in obstetrics & gynecology and the like.

The linear array and convex array may be involved in the foregoing one-dimensional transducer array.

As shown in FIG. 8, the main body 120 may be coupled with the head 113 of the phased array type. The transducer having the head 113 of the phased array type is capable of observing a body part in a narrow space like a space between ribs, and may for example be used in heart examination. It may be utilizable for breast, thyroid, musculoskeletal and the like diagnoses.

The phased array has a double- or multi-layered structure where the elements are arranged, and is included in the foregoing two-dimensional transducer array. The transducer element may be arranged in a linear line, or a curved line as necessary. Therefore, a frequency is ranged corresponding to the arranged form. Further, the two-dimensional phased transducer array appropriately delays the input time of the signals respectively input to the elements, and transmits the delayed ultrasound to the object, thereby using a plurality of echo signals to obtain a three-dimensional (3D) image.

Figure 9:
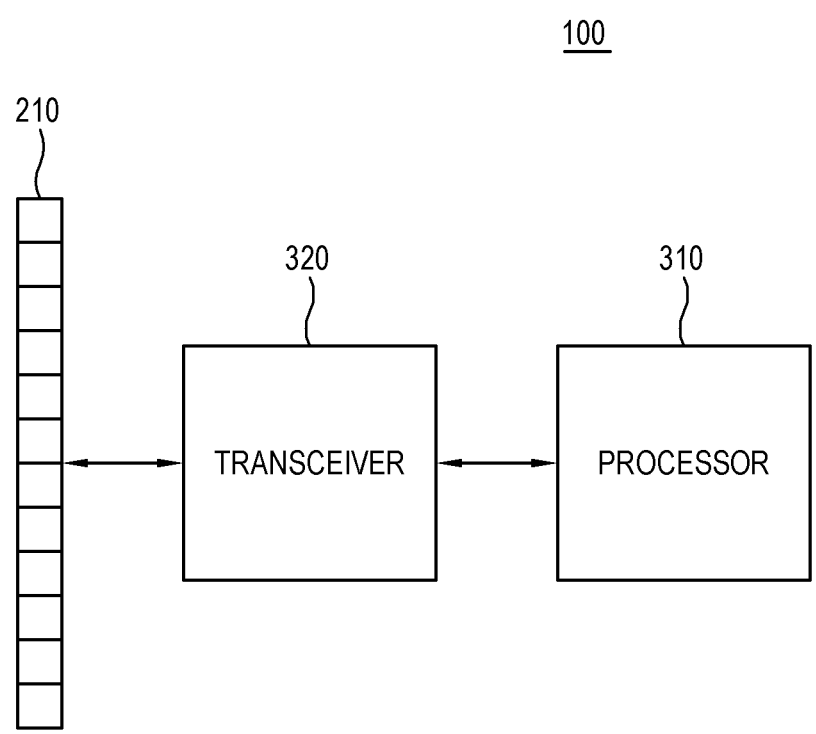
FIG. 9 is a block diagram of schematically illustrating the probe apparatus according to one embodiment of the present disclosure.

FIG. 9 is a block diagram of schematically illustrating the probe apparatus 100 according to one embodiment of the present disclosure.

In one embodiment, the probe apparatus 100 includes the main body 120, and the head 110 detachably provided in the main body 120. FIG. 9 illustrates that the head 110 including the transducer array 210, in which the plurality of elements are arranged in a predetermined form, is coupled to the main body 120.

Referring to FIG. 9, the probe apparatus 100 includes the transducer array 210 for outputting ultrasound for a diagnosis of an object. The transducer array 210 may be provided in the head 110 of the probe apparatus 100.

The probe apparatus 100, as shown in FIG. 9, may include the transceiver 320 for transceiving a signal to and from the transducer array 210 through a plurality of channels, and at least one processor 310 for controlling the transceiver 320. The processor 310 and the transceiver 320 may be provided in the main body 120 of the probe apparatus 100.

The transducer array 210 receives an electric signal from the transceiver 320, and emits ultrasound corresponding to the electric signal to the object. Further, the transducer array 210 transmits an electric signal converted from the ultrasound echo signal received from the object to the transceiver 320.

The processor 310 controls the transceiver 320 to output the electric signal before it is converted into the ultrasound signal in the transducer array 210. In one embodiment, the processor 310 adjusts data involved in the output electric signal, and controls the electric signal with the adjusted data to be converted to have characteristics corresponding to the probe type and output from the transducer array 210.

Specifically, in adjusting the data involved in the electric signal, the processor 310 may for example adjust at least one of data for turning on/off the transceiver 320, data for selecting a diagnosis mode, data about beamforming, and apodization data. Here, the data about the beamforming refers to data for focusing the ultrasound signal output through the transducer array 210 on a target point of the object. Further, the apodization data refers to data about a process for decreasing a high-degree diffraction image.

Therefore, the processor 310 adjusts various pieces of data about the transceiver 320, and controls the transceiver 320 to output an electric signal corresponding to the probe type of the transducer array 210. That is, the processor 310 operates in accordance with the probe types of the transducer array 210 of the head 110 mounted to the main body 120.

To this end, the processor 310 controls the transceiver 320 to transmit a predetermined test signal (hereinafter, referred to as a 'test tone') to the transducer array 210, determines the probe type corresponding to the transducer array 210 of the mounted head 110 based on a feedback signal received through the transceiver 320 in response to the test signal, and makes the probe apparatus 100 operate corresponding to the determined probe type.

Here, the processor 310 may sense whether the head 110 is mounted to the main body 120 through the first connector 230 and the second connector 330. That is, according to one exemplary embodiment, when it is sensed that the head 110 having the transducer array 210 of a predetermined probe type is mounted to the main body 120, the processor 310 transmits a predetermined test signal (or an alarm signal) to determine the probe type corresponding to the transducer array 210 of the mounted head 110.

The transceiver 320 transmits an electric signal to the transducer array 210 under control of the processor 310, and receives an electric signal corresponding to an echo signal from the transducer array 210.

In one exemplary embodiment, the transceiver 320 includes a multi-channel transceiver for transceiving a signal through the plurality of channels (i.e. transmission channels). The transceiver 320 may for example be materialized by a 64-channel transceiver, a 128-channel transceiver, and the like application specific integrated circuit (ASIC). Here, there are no limits to materialization of the transceiver 320, and the transceiver 320 may be materialized by various kinds of other elements.

The transceiver 320 may include at least one ASIC. For example, the transceiver 320 may include a plurality of (e.g. two) 64-channel transceivers.

The ASIC refers to a order integrated circuit to be used by a user for a specific purpose. In this embodiment, the ASIC operates as an analog front end (AFE).

In one exemplary embodiment, the transceiver 320 may be materialized such that a transmitter and a receiver are separated.

Hereinafter, it will be defined that each of the transceiver, the AFE and the ASIC has the same meaning as the transceiver 320.

Further, the processor 310 and the transceiver 320 of the probe apparatus 100 according to one embodiment of the present disclosure will be described in detail with reference to FIG. 10.

Figure 10:
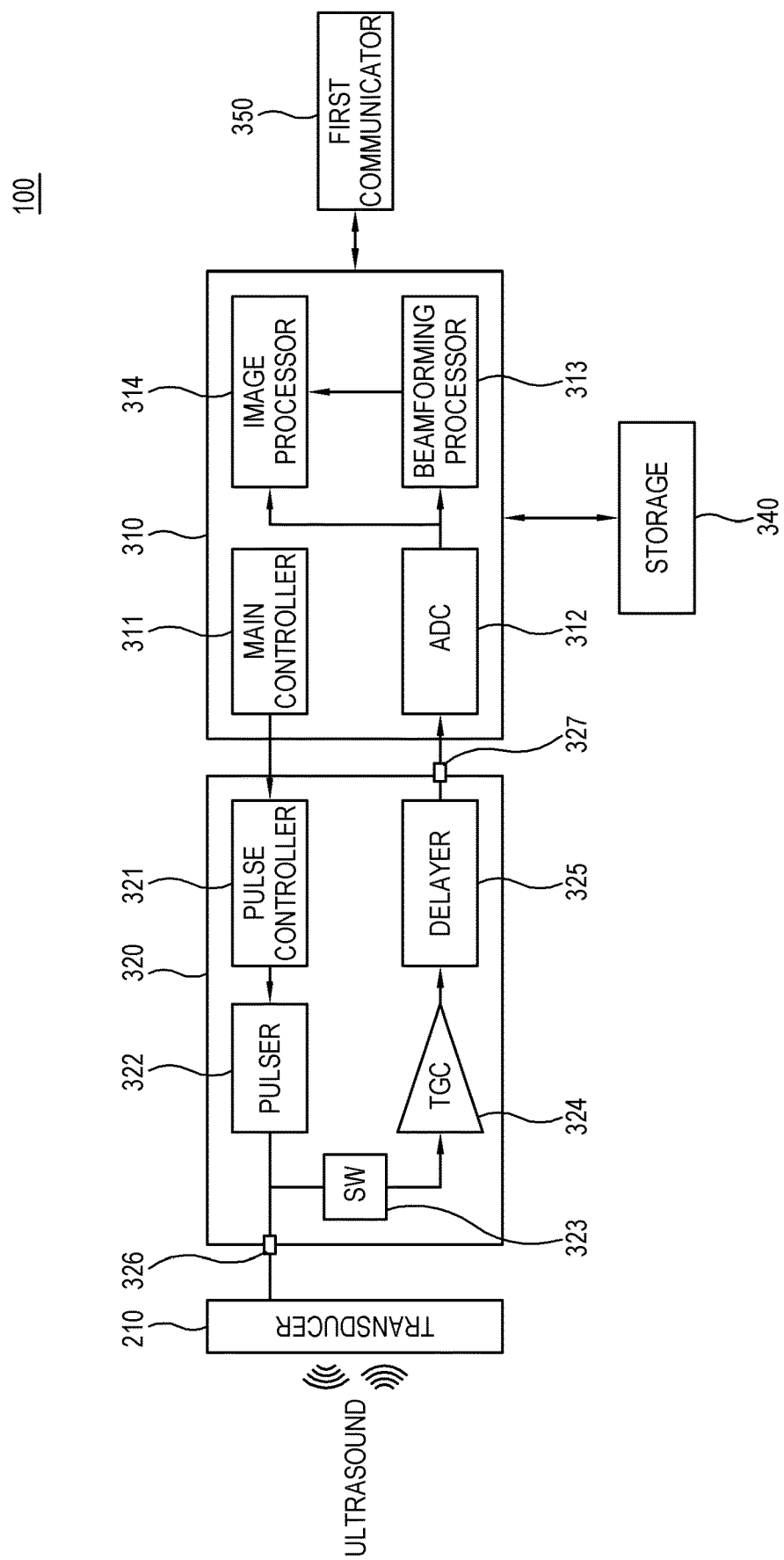
FIG. 10 is a block diagram of schematically illustrating elements of the probe apparatus shown in FIG. 9.

FIG. 10 is a block diagram of schematically illustrating elements of the probe apparatus 100 shown in FIG. 9.

As shown in FIG. 10, the probe apparatus 100 may further include a storage 340 configured to store data, and a first communicator 350 configured to communicate with an external device such as the display apparatus 400. However, all the illustrated elements are not essential, and other general-purpose elements may be further provided in addition to the illustrated elements.

The transceiver 320 supplies a driving signal to the transducer array 210 and receives the ultrasound echo signal from the transducer array 210. As shown in FIG. 10, the transceiver 320 may include a pulse controller 321, a pulser 322, a switch (SW) 323, a time gain compensator (TGC, or referred to as a 'TGC amplifier' 324, and a delayer 325.

The pulse controller 321 controls the driving signal based on the electric signal received from the processor 310 to be applied to the transducer array 210. The pulse controller 321 converts a digital signal received from a main controller 311 of the processor 310 to be described later into an analog signal, transmits the analog signal to the pulser 322, and controls operations of the pulser 322.

The pulse controller 321 receives a digital signal, which includes a pulse generated to be convertible into an ultrasound signal, from the processor 310. To this end, the main controller 311 of the processor 310 generates a rate pulse for forming transmission ultrasound based on a predetermined pulse repetition frequency (PRF). Such a generated rate pulse may be subjected to a delay time and a delay pattern for determining transmission directionality. Each rate pulse subjected to the delay time corresponds to each of the plurality of elements included in the transducer array 210.

Under control of the pulse controller 311, the pulser 322 applies a driving signal (or a driving pulse) to the transducer 210 at a timing corresponding to each rate pulse subjected to the delay time. In one exemplary embodiment, the pulser 322 may be materialized by a high-voltage (HV) pulser.

The switch 323 provides switching between transmission (tx) and reception (rx) using the plurality of channels. By the switch 323, each channel of the transceiver 320 performs either of transmitting or receiving a signal.

In one exemplary embodiment, the transceiver 320 transmits the test signal through one channel among the plurality of channels, and receives a feedback signal through a channel excluding the channel used in transmitting the test signal among the plurality of channels.

The time gain compensator 324 amplifies the ultrasound echo signal received from the transducer 210 and compensates for a time gain. The time gain compensator (TGC) is a parameter to compensate for attenuation of the ultrasound echo in proportion to diagnosis depth, and may influence quality of an image in the ultrasound diagnosis system. In this embodiment, the ultrasound echo signal passed through the time gain compensator 324 can provide an ultrasound image improved in the image quality even in a deep region.

The delayer 325 applies a delay time for determining reception directionality to the ultrasound echo signal. The delayer 325 may be configured to generate ultrasound data based on the sum of signals subjected to the delay time. In one exemplary embodiment, it is possible to emphasize reflected components in a direction determined corresponding to the reception directionality by the summing process.

The transceiver 320 may transmit and receive a signal to and from the transducer 210 and the processor 310 through input/output (IO) pads 326 and 327.

The plurality of channels in the transceiver 320 may correspond to the arranged elements of the transducer array 210, respectively. Here, the number of channels may be equal to or greater than the number of elements in the transducer array 210.

The number of transducer arrays 210 may be varied depending on the probe types. Therefore, the number of channels in the transceiver 320 may be equal to or greater than the maximum number of elements arranged in the transducer array 210 according to the probe types among the heads 111, 112 and 113 mountable to the main body 120.

As a kind of response signal to the test signal, a feedback signal received through the transceiver 320 in response to the test signal includes an interference signal (e.g. a crosstalk signal). That is, the feedback signal is a kind of feedback signal (or a feedback interference signal, and refers to that at least a part of the test signal is returned to and has an influence on an input side, i.e. the transceiver 320.

In one exemplary embodiment, the transceiver 320 transmits the test signal though one channel among the plurality of channels (Tx), and receives the feedback signal, i.e. the interference signal through other channels except the channel for transmitting the test signal (Rx).

The processor 310 performs control with regard to various elements of the probe apparatus 100. For example, the processor 310 proceeds with image processing of the image processor 314, and performs control corresponding to a user's input, thereby controlling general operations of the probe apparatus 100.

The processor 310, as shown in FIG. 10, includes the main controller 311, an analog digital converter (ADC) 312, a beamforming processor 313 and an image processor 314. Further, although it is not shown, the processor 310 may include the firth to nth interfaces, and the processor 310 is connected to various elements inside the probe apparatus 100 through the first to nth interfaces. In one exemplary embodiment, one of the interfaces may be used as a network interface connecting with an external device through a network. In this case, the network interface is equivalent to the first communicator 350 to be described later.

The main controller 311 controls general operations of the probe apparatus 100. The main controller 311 loads a program from a nonvolatile memory (e.g. a read only memory (ROM)) to a volatile memory (e.g. a random access memory (RAM), and executes the loaded program. Specifically, an operating system (O/S) stored in the probe apparatus 100, e.g. the storage 340, the ROM in the processor 310, etc. is used in booting. Further, the main controller 311 may use various program, content, data, etc. stored in the storage 340 to operate various operations.

The processor 310 may include the ROM (not shown), the RAM (not shown), etc., and the ROM (not shown) is stored with a command set or the like for booting up the system. When a turn-on command is input to supply power, the main controller 311 copies the O/S stored in the storage 340 to the RAM (not shown) in response to a command stored in the ROM (not shown), and executes the O/S to boot up the system. When the system is completely booted up, the main controller 311 copies various application programs stored in the storage 340 to the RAM (not shown), and executes the application program copied to the RAM (not shown), thereby performing various operations.

In this exemplary embodiment, the processor 310 includes at least one general-purpose processor such as a central processing unit (CPU), an application processor (AP), and a microcomputer (MICOM), and loads and executes a program corresponding to a predetermined algorithm from the ROM to the RAM, thereby implementing various operations of the probe apparatus 100.

When the processor 310 includes the CPU, the main controller 311 is equivalent to the CPU.

The processor 310 may include a single-core processor, a dual-core processor, a triple-core processor, a quad-core processor, and the like multiple-core processor. The processor may include a plurality of processors, for example, a main processor and a sub processor. The sub processor is provided to operate in a standby mode (hereinafter, referred to as a 'sleep mode') in which it is supplied with only standby power and does not operate as the probe apparatus 100.

The processor, the ROM and the RAM as described above may be connected to one another by an internal bus.

In one exemplary embodiment, the processor 310 may be materialized by a program for implementing a specific function supported in the probe apparatus 100, and an integrated circuit (IC), e.g., a mixed signal IC, provided as a processor dedicated for executing the program.

The ADC 312 converts a signal received from the transceiver 320 into a digital signal by analog-digital conversion. The ADC 312 converts a plurality of received signals corresponding to a plurality of focusing points sequentially provided from the transducer array 210 into a plurality of digital signals by the analog-digital conversion.

The beamforming processor (or a beam-former) 313 may perform beamforming to focus the ultrasound signal output through the transducer array 210 to be focused on the focusing point based on at least one of the depth, size and position of the focusing point. In one exemplary embodiment, the beamforming processor 131 may perform pre-processing, for example, gain control, etc. with regard to the ultrasound signal for the generation of the ultrasound image performed in the image processor 314.

The image processor 314 generates the ultrasound image based on the ultrasound echo signal received through the transducer array 210. In one exemplary embodiment, the image processor 314 may support a plurality of modes, and generate the ultrasound image corresponding to each mode.

The kinds of ultrasound image is assorted into a brightness mode (or B mode) image in which the strength of the ultrasound echo signal reflected from the object is represented with the brightness, a Doppler mode (or D mode or PW-Doppler mode) image in which an image of an moving object is represented in a spectrum form using the Doppler effect, a motion mode (or M mode) image in which a motion of an object is represented at a certain position as time goes on, an elastic mode image in which a difference between when an object is pressed or when the object is not pressed is represented on an image, a color mode image (or C mode) in which a speed of a moving object is represented with color using the Doppler effect, etc. Further, the kind of ultrasound image may be assorted into images of 1D, 2D, 3D, 4D or the like mode dimension in accordance with the dimensions to be displayed.

For example, in case of the B mode, the image processor 314 applies a filtering process to a signal received from the probe head 110 to remove noise components, and applies a scan conversion process to generate a B-mode ultrasound image including a plurality of scan lines.

Further, in case of the Doppler image, the image processor 314 adjusts a gain of a signal received from the probe head 110 based on a preset color gain, and performs a frequency analysis to obtain information about movement of an object from the adjusted signal, thereby generating Doppler data. Further, the image processor 314 may generate a Doppler image showing the movement of the object based on the Doppler data. The Doppler image shows information about the average speed, distribution, power component, etc. of the object, with color (i.e. a color Doppler image) or a frequency spectrum (i.e. a spectrum Doppler image).

The Doppler image may include not only a Doppler image corresponding to a still image, but also a Doppler image corresponding to a moving image and the like successive images. Further, the Doppler image may include both a Doppler image (2D Doppler) for a plane, and a Doppler image (3D Doppler) for a cubic space. Further, the Doppler image may include a blood flow Doppler image (or called a color Doppler image) showing a flow of blood, and a tissue Doppler image showing movement of tissue.

Further, in case of the 3D image, the image processor 314 forms volume data from a signal received from the probe head 110, and applies volume rendering to the volume data, thereby generating a 3D ultrasound image.

The volume rendering is a technique for generating a 2D projection image with regard to a 3D discretely sampled data set such as the volume data. For example, the image processor 314 may perform a volume rendering process through a ray casting method of calculating reflected light by casting a virtual ray to an object located in a virtual space.

In one embodiment, the probe apparatus 100 may be materialized to provide an ultrasound medical image in real time with regard to an interesting volume of an object. For example, when organs are transformed and displaced by body activities of an object, a medical image displayed on the display apparatus 400 in real time is also varied. In this case, the processor 310 may further include real-time control (not shown) for real-time display.

The storage 340 is configured to store data without limitations under control of the processor 310. The storage 340 may be provided as a built-in memory in the main body 120 of the probe apparatus 100, or an external storage device as necessary. Further, in the probe apparatus 100 according to the present disclosure, the storage 340 may be materialized as a memory provided inside the processor 310. Here, the storage 440 of the display apparatus 400 to be described later may be an example of an external storage device. In this case, the processor 310 may access the external storage device 440 through the first communicator 350.

The storage 340 may be a flash memory or the like nonvolatile storage medium provided inside or outside the probe apparatus 100, and accessed by the processor 310 to perform reading/recording/modifying/deleting/updating the data.

The data stored in the storage 340 may for example include not only an operating system for driving the probe apparatus 100, but also various applications executable in this operating system, data, etc.

The storage 340 in this embodiment may store information for determining the probe type of the transducer array 210. Specifically, the storage 340 may store parameter information corresponding to each probe type of the plurality of heads 110 connectable to the main body 120.

Figure 11:
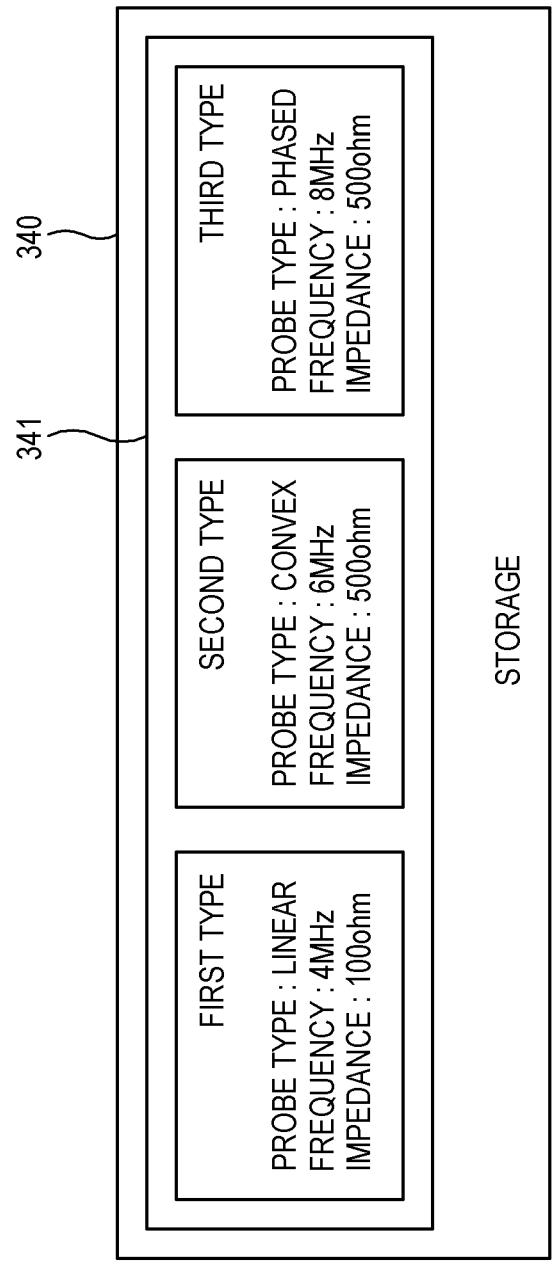
FIG. 11 is a view of illustrating an example of information stored in a storage of the probe apparatus according to one embodiment of the present disclosure.

FIG. 11 is a view of illustrating an example of information stored in the storage 340 of the probe apparatus 100 according to one embodiment of the present disclosure.

As shown in FIG. 11, the storage 340 involves a table 341 stored with information about a plurality of probe types, for example, a first type, a second type, a third type. FIG. 11 illustrates the information about the probe types by way of example. As necessary, a probe type may be newly added or deleted from the table 341, and information corresponding to a specific type may be added, deleted and modified.

The processor 310 may determine the probe type corresponding to the transducer array 210 of the head mounted to the main body 120 of the probe apparatus 100 based on information stored in the storage 340. Further, the processor 310 loads parameter information corresponding to the determined probe type from the storage 340, and set a parameter for operating the probe apparatus 100 based on the loaded information.

In one exemplary embodiment, the storage 340 may store various pieces of data related to the ultrasound image data. For example, the storage 340 may store at least one piece of image data generated based on an ultrasound signal received through the transducer array 210, and the image data stored in the storage 340 may be displayed by the display apparatus 400.

In one exemplary embodiment, an ultrasound image generated by the image processor 314 is transmitted to the display apparatus 400 through the first communicator 350, and displayed for a user as an ultrasound medical the image on the display apparatus 400.

The first communicator 350 may include at least one of various wireless communication modules such as a short-range communication with a predetermined frequency, Wi-Fi, Wi-Fi Direct, ultra-wideband (UWB), Bluetooth, radio frequency (RF), Zigbee, wireless local area network (LAN), near field communication (NFC), etc. That is, according to one embodiment of the present disclosure, the first communicator 350 may support a plurality of wireless communication modules, for example, both 60 GHz near field communication and Wi-Fi.

In one exemplary embodiment, the first communicator 350 may include a wired communication module. That is, the first communicator 350 may be materialized to communicate with external devices including the display apparatus 400 through at least one among the wired or wireless communication modules.

The first communicator 350 may be internally provided in the main body 120 of the probe apparatus 100, or materialized in the form of a dongle or module and detachably connected to the connector (not shown) of the probe apparatus 100. Alternatively, the first communicator 350 may include I/O ports for connecting human interface devices (HID).

In one embodiment, the probe apparatus 100 may be directly connected to the display apparatus 400 via the first communicator 350. In another embodiment, the first communicator 350 may include the connector for connection with the external storage medium capable of storing a medical image.

In one exemplary embodiment, the first communicator 350 may exchange data with a hospital server connected through a picture archiving and communication system (PACS) or other medical devices in a hospital, and performs data communication in accordance with standards of digital imaging and communications in medicine (DICOM). That is, the first communicator 350 is connected to the wired or wireless network and transmits/receives data related to a diagnosis of an object.

Further, the first communicator 350 may perform data communication with a portable device (terminal) or the like of a user or a patient as well as the display apparatus 400 or the server in the hospital. Further, defects in equipment and quality control information are transmitted to a system administrator or service representative though the network, and it is possible to get a feedback on them.

The display apparatus 400 may generate and display an ultrasound screen based on an ultrasound image received from the probe apparatus 100.

Figure 12:
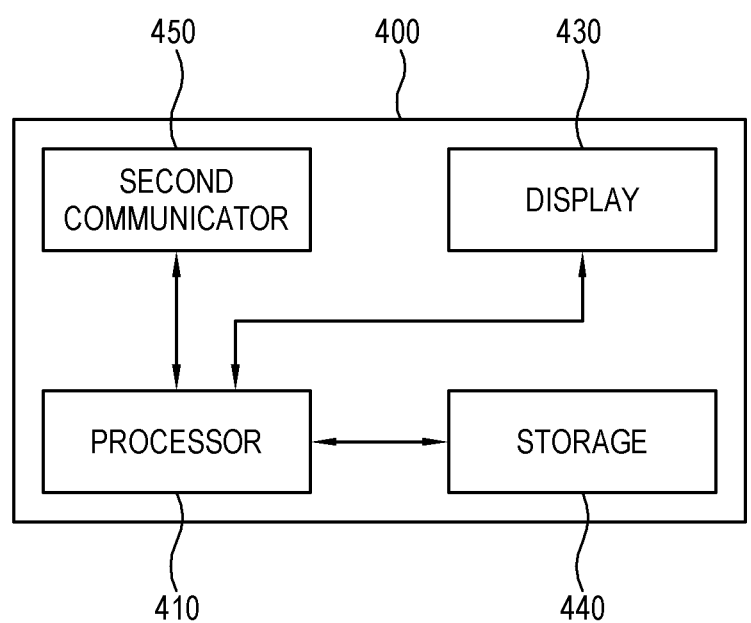
FIG. 12 is a block diagram of schematically illustrating elements of a display apparatus according to one embodiment of the present disclosure.

FIG. 12 is a block diagram of schematically illustrating elements of the display device 400 according to one embodiment of the present disclosure, As shown in FIG. 12, the display apparatus 400 may include at least one processor 410, a display 430, a storage 440 and a second communicator 450.

The processor 410 controls general operations of the display apparatus 400.

For example, the display 430 displays an application related to an ultrasound diagnosis. For example, the display 430 may display a menu or a guide needed in the ultrasound diagnosis using the probe apparatus 100. Further, the display 430 may display an image obtained from the probe apparatus 100 during the ultrasound diagnosis, and a user interface (UI, hereinafter also referred to as a GUI) for helping a user's control.

FIG. 12 shows an example that one display 430 is provided in the display apparatus 400, but the present disclosure is not limited thereto. Alternatively, the display apparatus 400 may be configured to include a plurality of displays, for example, a main display and a sub display.

The processor 410 processes an ultrasound image to be displayed on the display 430. Specifically, the processor 410 processes a signal received and obtained from the probe apparatus 100 through the second communicator 450 and makes an image based on image data to be displayable on the display 430.

In one exemplary embodiment, the processor 410 includes an operator (not shown) and a renderer (not shown), and employs them to generate an ultrasound screen including various objects, such as an icon, an image, a text and the like. The operator computes attribute values such as coordinates, shape, size, color, and the like for displaying the objects in accordance with layouts of a screen based on a received control command. The renderer generates a screen of various layouts including an object based on the attribute values computed in the operator. The screen generated in the renderer may be displayed through the display apparatus 400. Here, the renderer may correspond to a GPU to be described later.

In one exemplary embodiment, the processor 410 may perform at least a part of image processing performed in the image processor 314 of the probe apparatus 100.

That is, in one embodiment of the present disclosure shown in FIGS. 10 and 11, the ultrasound image generated in the image processor 314 of the probe apparatus 100 is transmitted to the display apparatus 400, but the present disclosure is not limited thereto. For example, the display apparatus 400 may receive an ultrasound echo signal, which has been converted into a digital signal, from the probe apparatus 100, and generate an ultrasound image corresponding to the B mode, the CD (color Doppler) mode, the D (PW Doppler) mode, etc. In this case, the processor 410 of the display apparatus 400 may include the image processors for supporting the diagnosis modes, respectively.

The processor 410 performs control for various elements of the display apparatus 400. For example, the controller 400 performs signal transceiving through the second communicator 450, control operations corresponding to command input by a user through the GUI, thereby controlling general operations of the display apparatus 400.

The display apparatus 400 includes at least one processor 410. At least one processor 410 loads a program from a nonvolatile memory (e.g. ROM) storing the program to a volatile memory (e.g. RAM), and executes the program.

The processor 410 according to this embodiment includes at least one general-purpose processor such as a central processing unit (CPU), an application processor (AP), and a microcomputer (MICOM), and loads and executes a program corresponding to a predetermined algorithm from the ROM to the RAM, thereby implementing various operations of the medical image display apparatus 1000.

When the display apparatus 400 includes a single processor, e.g. a CPU, the CPU may be provided to implement various functions performable in the display apparatus 400, such as various imaging processes for the ultrasound medical image to be displayed on the display 1020, for example, selection of a protocol to be applied, imaging control corresponding to the selected protocol, following a command received through the user input 1040, control of wired/wireless network communication with an external device, etc.

The processor 410 may include a single-core processor, a dual-core processor, a triple-core processor, a quad-core processor, and the like multiple-core processor. The processor may include a plurality of processors, for example, a main processor and a sub processor. The sub processor is provided to operate in a standby mode (hereinafter, referred to as a sleep mode) in which it is supplied with only standby power and does not operate as the display apparatus 400.

The processor, the ROM and the RAM may be connected to one another by an internal bus.

According to one embodiment of the present disclosure, when the display apparatus 400 is materialized by a laptop or desktop computer, the processor 410 may be provided in plural. The plurality of processors may be provided in a main body, and may further include a central processing unit (CPU) operating as a main controller, and a graphic processing unit (GPU, not shown) for a graphic process. Further, according to another embodiment, when the display apparatus 400 is materialized by a portable terminal such as a smart phone, a smart pad, etc., a single processor may also perform even the function of the GPU. For example, the processor may be materialized by a system on chip (SoC) where the core and the GPU are coupled.

The display 430 displays an image based on an image signal processed by the processor 410. There are no limits to the materialization of the display 430, and the display 430 may be materialized by various display types, for example, liquid crystal, plasma, a light-emitting diode, an organic light-emitting diode, a surface-conduction electron-emitter, a carbon nano-tube, nano-crystal, etc.

The display 430 may include additional elements in accordance with its materialization. For example, when the display 430 is a liquid crystal type, the display 430 includes a liquid crystal display (LCD) panel (not shown), a backlight unit (not shown) for emitting light the panel, and a panel driving substrate (not shown) for driving the panel (not shown).

The display 430 displays various user interfaces UI including menu items for the display apparatus 400. Further, the display 430 displays a pointing cursor, that is, a pointer that points to a user's input position.

In one exemplary embodiment, the display 430 may be materialized by a touch screen. In this case, the display apparatus 400 may receive various gesture inputs as a touch input to the touch screen.

The touch screen may receive a single touch or a multi touch. The touch screen may for example be materialized by a resistive type, a capacitive type, an infrared type, or an acoustic wave type. In this embodiment, the display 430 may be configured so that a gesture input onto the touch screen can be made using a user's body (e.g. a finger) or a touch pen given as a touch tool (e.g. a pointing device, a stylus, a haptic pen, etc.).

The storage 440 stores data without limitations under control of the processor 410. The storage 440 may be materialized by a flash memory, a hard disc drive or the like nonvolatile storage medium. The storage 4400 is accessed by the processor 410 to read/record/modify/delete/update/ etc. with regard to the data.

The data stored in the storage 440 may for example include not only an operating system (OS) for driving the medical image display device 1000, but also various applications executable in this operating system, image data, appended data, etc.

In one exemplary embodiment, the storage 440 may be configured to store various pieces of data related to the medical image. Specifically, the storage 440 is configured to store at least one piece of image data generated by data received from the probe apparatus 100, and/or at least one piece of image data received from the exterior. The image data stored in the storage 440 is displayed by the display 430.

In this embodiment, the storage 440 of the display apparatus 400 may be configured to store at least a part of the parameter information corresponding to each probe type and information for determining the probe type of the transducer array 210. That is, the information of FIG. 11 is stored in the storage 440 of the display apparatus 400, and transmitted to the probe apparatus 100 through the second communicator 450.

The second communicator 450 may include at least one of various wireless communication modules such as a short-range communication at a predetermined frequency (e.g. 60 GHz), Wi-Fi, Wi-Fi Direct, ultra-wideband (UWB), Bluetooth, radio frequency (RF), Zigbee, wireless local area network (LAN), near field communication (NFC), etc. That is, according to one embodiment of the present disclosure, the second communicator 450 may support a plurality of wireless communication modules, for example, both the short-range communication at 30 GHz and Wi-Fi.

In one exemplary embodiment, the second communicator 450 may include a wired communication module. That is, the second communicator 450 may be configured to perform communication with the display apparatus 400 and the like external devices by at least one of the wired or wireless communication modules.

In this embodiment, the second communicator 450 is provided corresponding to the first communicator 350, and transmit and receive data to and from the probe apparatus 100.

The second communicator 450 may be internally provided in the display apparatus 400, or materialized in the form of a dongle or module and detachably connected to the connector (not shown) of the display apparatus 400. Alternatively, the second communicator 450 may include I/O ports for connecting human interface devices (HID).

In one embodiment, the display apparatus 400 may be directly connected to the probe apparatus 100 or other medical devices via the second communicator 450. In another embodiment, the second communicator 450 may include the connector for connection with the external storage medium capable of storing a medical image.

In one exemplary embodiment, the second communicator 450 may exchange data with a hospital server connected through a picture archiving and communication system (PACS) or other medical devices (e.g. an MRI device, a CT device, etc.) in a hospital, and performs data communication in accordance with standards of digital imaging and communications in medicine (DICOM). That is, the second communicator 450 is connected to the wired or wireless network and transmits/receives data related to a diagnosis of an object.

Further, the second communicator 450 may perform data communication with a portable device (terminal) or the like of a user or a patient as well as the display apparatus 400, the server in the hospital, or other medical devices. Further, defects in equipment and quality control information are transmitted to a system administrator or service representative though the network, and it is possible to get a feedback on them.

By the way, although it is not shown, the display apparatus 400 in one exemplary embodiment may further include a user input capable of receiving a user's command. The user input may include a button for allowing a user to directly control the display apparatus 400, a keypad, a switch, a dial, or a graphic user interface (GUI) displayed on the display 430. In one exemplary embodiment of the present disclosure, the user input may include a touch screen provided on the display 430.

In one embodiment, the processor 410 of the display apparatus 400 may receive a user command for executing a predetermined application as a platform capable of analyzing an ultrasound medical image through the user input. In one exemplary embodiment, by executing an application, an input region in which various buttons are displayed as a UI for allowing a user' selection, and a display region in which the medical image is displayed may be displayed on the display 430. The input region may be displayed on a predetermined position, e.g. in a lower position of the display 430.

A user can load an ultrasound image obtained from the probe apparatus 100 through the UI of the input region of the application, and the loaded ultrasound image is provided to a user through the display region of the application. Further, a user may issue a command for registration between the first medical image and the second medical image in the executed application.

In one embodiment of the present disclosure, the probe apparatus 100 and/or the display apparatus 400 may be installed with an application for an ultrasound diagnosis, i.e. software, to be driven by at least one processor 110 and 310, i.e. hardware. That is, operations to be described below may be implemented by execution of software to be driven by the processor 110 or 310.

Below, various embodiments of determining and using the probe type in the medical probe apparatus 100 will be described in more detail with reference to the accompanying drawings.

FIGS. 13 to 19 are views for illustrating a procedure of determining the probe type of the transducer array 210 in the probe apparatus 100 according to one embodiment of the present disclosure.

Figure 13:
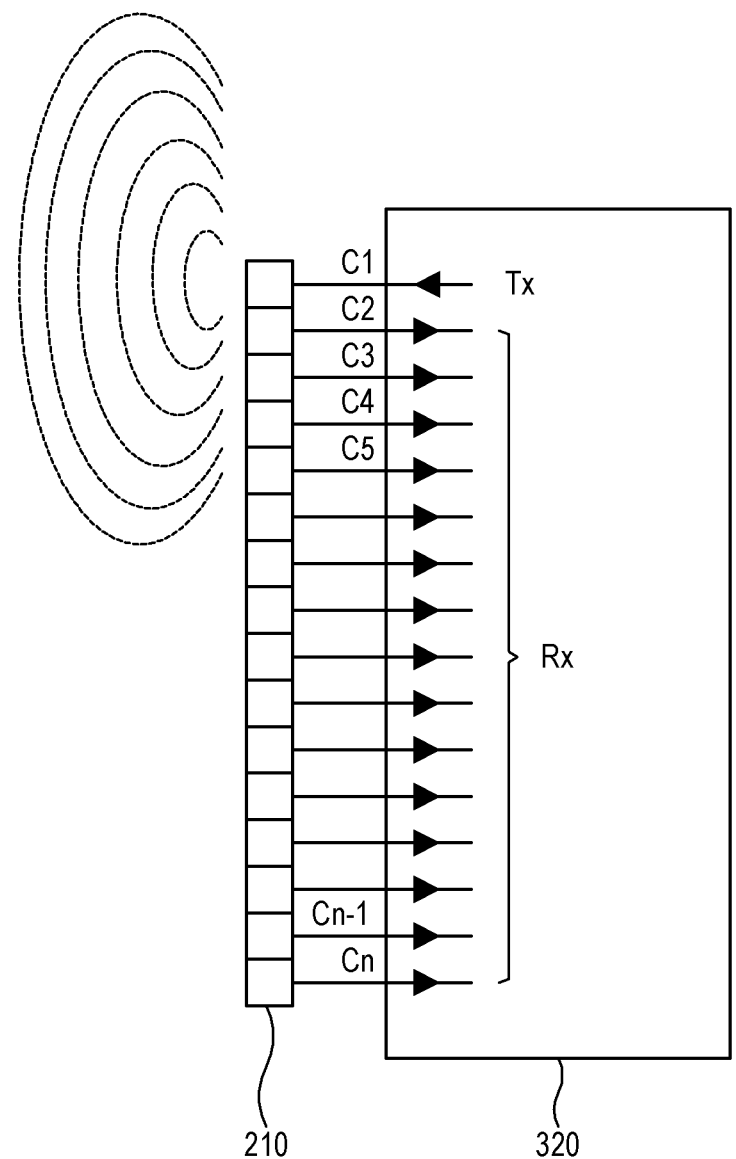

As shown in FIG. 13, the transceiver 320 of the probe apparatus 100 transmits a predetermined test signal Tx to the transducer array 210, and receives a feedback signal Rx in response to the transmitted test signal, under control of the processor 310

Here, as shown in FIG. 13, the transceiver 320 may transmit the test signal Tx through one channel C1 among the plurality of channels C1, C2, C3, . . . , Cn–1, Cn, and receive the feedback signal Rx through channels C2, C3, . . . , Cn–1, Cn except the channel C1 used in transmitting the test signal among the plurality of channels C1, C2, C3, . . . , Cn–1, Cn.

In one exemplary embodiment, the received feedback signal Rx becomes channel-channel crosstalk between the channels, which is generated in response to the test signal Tx.

Figure 14A:
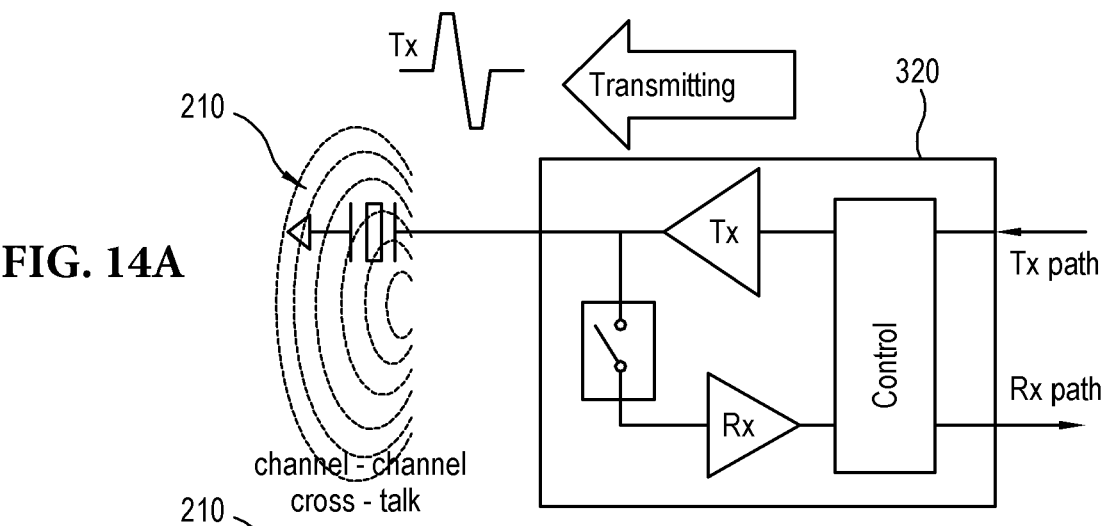

Specifically, referring to FIG. 14(a), the transceiver 320 transmits the test signal Tx to the transducer array 210 through a predetermined channel (e.g. C1). Here, as shown in FIG. 14(a), the switch 323 is turned off so that the test signal can be transmitted through the corresponding channel C1.

Figure 14B:
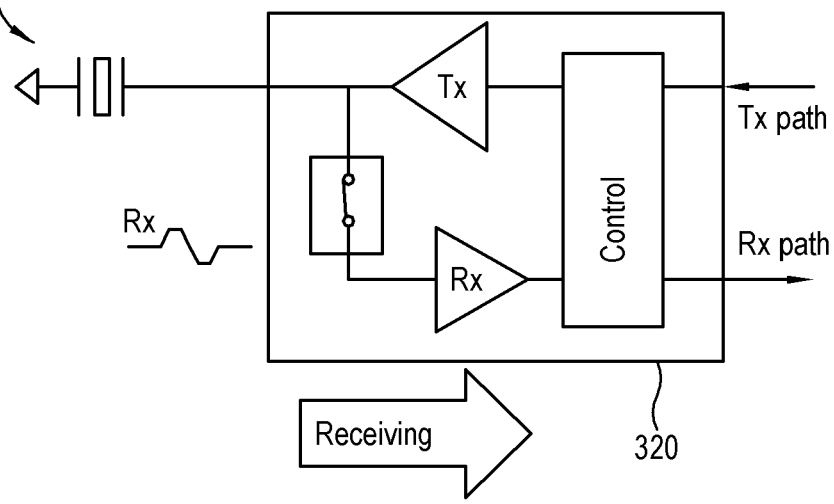

Further, as shown in FIG. 14(b), the response signals to the test signal Tx, that is, the feedback signals Rx are received in sequence through the other channels e.g. C2, C3, . . . , Cn–1, Cn. Here, as shown in FIG. 14(b), the switch 323 is turned on so that the feedback signal can be received through the corresponding channels C2, C3, . . . , Cn–1, Cn.

That is, (a) and (b) of FIG. 14 conceptually illustrate that either of transmission or reception of a signal is carried out through the specific channel.

The processor 310 determines the probe type corresponding to the transducer array 210 of the mounted head 110, based on the feedback signal received through the other channels C2, C3, . . . , Cn–1, Cn in response to the test signal transmitted through the predetermined channel C1, so that the probe apparatus 100 can operate corresponding to the determined probe type.

In one exemplary embodiment, the processor 310 may determine the probe type based on a level change pattern, i.e. the pattern of the feedback signals received through the plurality of channels C2, C3, . . . Cn–1, Cn in sequence from the channel C2 adjacent to the channel C1 through which the test signal is transmitted. Here, the determined probe type corresponds to the element arranged shape of the transducer array 210.

Figure 16:
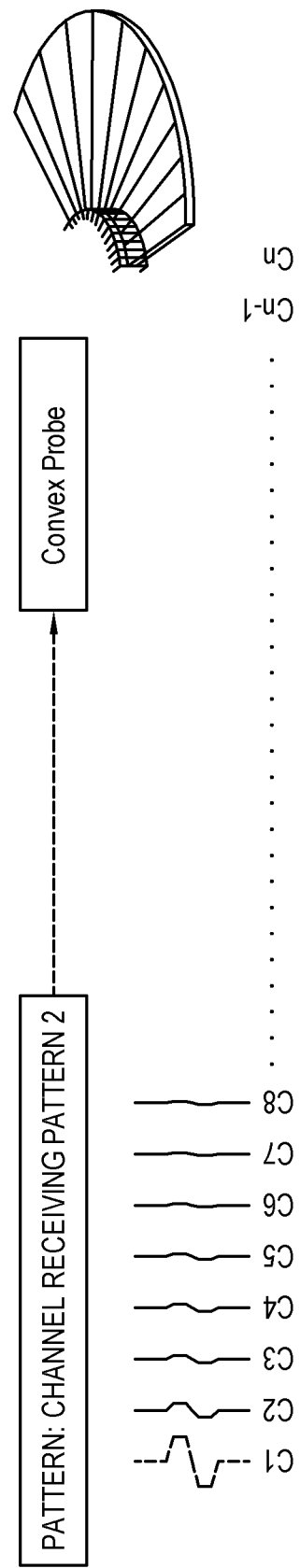
Figure 17:
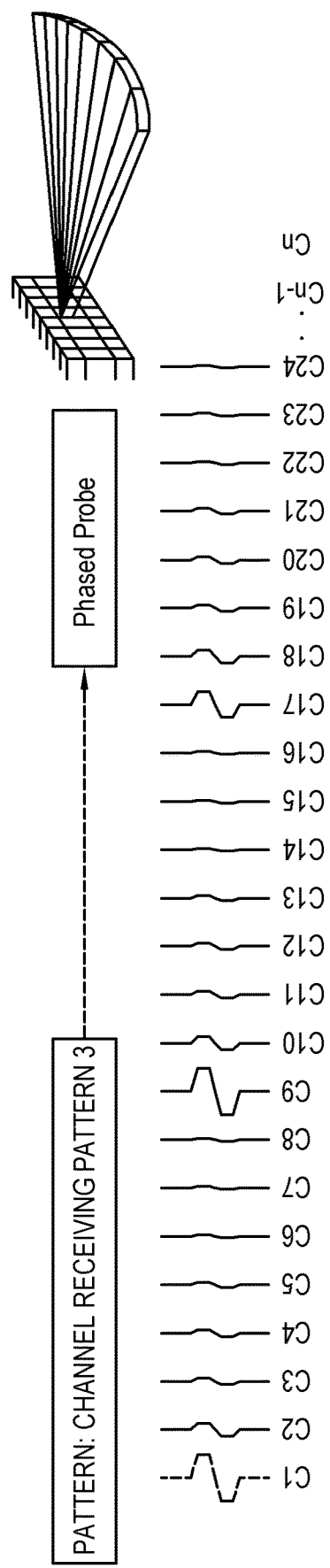

FIGS. 15 to 17 illustrate example of level change patterns of the feedback signals sequentially received corresponding to the probe type.

FIG. 13 and FIGS. 15 to 17 illustrate an example where the test signal is transmitted for determining the probe type through the first channel C1, and the feedback signals are received through other channels C2, C3, . . . , Cn–1, Cn, but the present disclosure is not limited thereto. That is, according to the present disclosure, it is possible to transmit the test signal through not only the first channel C1 but also any other channels of the transceiver 320, and it is thus possible to receive a corresponding feedback signal through at least one different channels.

Referring to FIG. 15, in case where the element arranged shape of the transducer array 210 forms a linear probe, it is ascertained that the level of the feedback signal received in sequence from the adjacent channel C2 in response to the test signal transmitted through the first channel C1 is gradually decreased. In this embodiment, the gradually decreased level of the feedback signal as shown in FIG. 15 will be defined as a first pattern.

In one exemplary embodiment, the processor 310 may determine the probe type of the transducer array 210 based on information stored in the storage 340. For example, the storage 340 may be configured to store the feedback signal having the first pattern to be matched with the first type of FIG. 11 where the probe type corresponds to a linear type.

When it is sensed that the feedback signals received through the channels of the transceiver 320 are matched with the first pattern, the probe type of the transducer array 210 of the head 110 mounted to the main body 120 is determined as the linear type, i.e. the first type, and the probe apparatus 100 operates corresponding to the determined probe type.

To this end, the processor 310 may set a parameter for making the probe apparatus 100 operate corresponding to the determined probe type.

In one exemplary embodiment, the processor 310 may set the parameter for operation corresponding to the probe type based on the information stored in the storage 340. Specifically, the storage 340 may be configured to store parameter information corresponding to a plurality of probe types as illustrated in FIG. 11, and the processor 310 loads the information corresponding to the determined probe type from the storage 340 and sets each parameter value to correspond to the loaded information.

For example, as shown in FIG. 15, when the probe type of the transducer array 210 is determined as the linear probe, that is, the first type, the processor 310 loads frequency and impedance values as the parameter information corresponding to the first type and sets the probe apparatus 100 to operate with these values.

Accordingly, a user does not have to input setting values one by one before using the device 100, and the probe apparatus 100 operates with the automatically optimized settings.

Referring to FIG. 16, in case where the element arranged shape of the transducer array 21 forms a convex probe, it is ascertained that the level of the feedback signal received in sequence from the adjacent channel C2 in response to the test signal transmitted through the first channel C1 is gradually decreased. Here, the decrease in the level of the convex probe is rapider than that of the linear probe of FIG. 15. In this embodiment, the rapidly decreased level of the feedback signal as shown in FIG. 16 will be defined as a second pattern.

The processor 310 may determine the probe type of the transducer array 210 based on information stored in the storage 340. For example, the storage 340 may be configured to store the feedback signal having the second pattern to be matched with the second type of FIG. 11 where the probe type corresponds to a curved type.

When it is sensed that the feedback signals received through the channels of the transceiver 320 are matched with the second pattern, the processor 310 determines the probe type of the transducer array 210 of the head 110 mounted to the main body 120 as the curved type, i.e. the second type, and makes the probe apparatus 100 operate corresponding to the determined probe type.

To this end, like the embodiment of FIG. 15, the processor 310 may set the parameter for making the probe apparatus 100 operate corresponding to the determined probe type, and employs the information stored in the storage 340.

For example, as shown in FIG. 16, when the transducer array 210 is determined as the convex probe, i.e. the second type, the processor 310 loads frequency and impedance values as the parameter information corresponding to the second type and sets the probe apparatus 100 to operate with these values.

Referring to FIG. 17, in case where the element arranged shape of the transducer array 210 forms a phased probe, it is ascertained that the level of the feedback signal received in sequence from the adjacent channel C2 in response to the test signal transmitted through the first channel C1 is periodically decreased. In this embodiment, the periodically decreased level of the feedback signal as shown in FIG. 17 will be defined as a third pattern.

The processor 310 may determine the probe type of the transducer array 210 based on information stored in the storage 340. For example, the storage 340 may be configured to store the feedback signal having the third pattern to be matched with the third type of FIG. 11 where the probe type corresponds to a multi-layered type.

When it is sensed that the feedback signals received through the channels of the transceiver 320 are matched with the third pattern, the processor 310 determines the probe type of the transducer array 210 of the head 110 mounted to the main body 120 as the phased type, i.e. the second type, and makes the probe apparatus 100 operate corresponding to the determined probe type, i.e. the third type.

To this end, like the embodiments of FIGS. 15 and 16, the processor 310 may set a parameter for making the probe apparatus 100 operate corresponding to the determined probe type, and may employ the information stored in the storage 340.

For example, as shown in FIG. 17, when the probe type of the transducer array 210 is determined as the phased probe, that is, the third type, the processor 310 loads frequency and impedance values as the parameter information corresponding to the third type and sets the probe apparatus 100 to operate with these values.

By the way, in the foregoing embodiments of the present disclosure, the transducer array 210 has three probe types, and each probe type is determined based on the level change pattern of the feedback signal, but not limited thereto. In other words, there are no limits to the probe type of the present disclosure.

Alternatively, the phased type may be varied in the number of layers and the array pattern differently from those of FIG. 17, and the processor 310 may determine the probe type based on the level change patterns of the feedback signal received in accordance with the types.

Further, there are no needs of sensing the feedback signal received from all the other channels C2, C3, . . . , Cn−1, Cn except the transmission channel. Alternatively, the pattern may be grasped by receiving the feedback signal through channels (e.g. five, eight and ten channels) corresponding to a preset number of channels. Here, the number of channels for sensing the feedback signal in the processor 310 may be variously set.

In one exemplary embodiment, a user may be notified of the foregoing determination results through the display 430.

Figure 18:
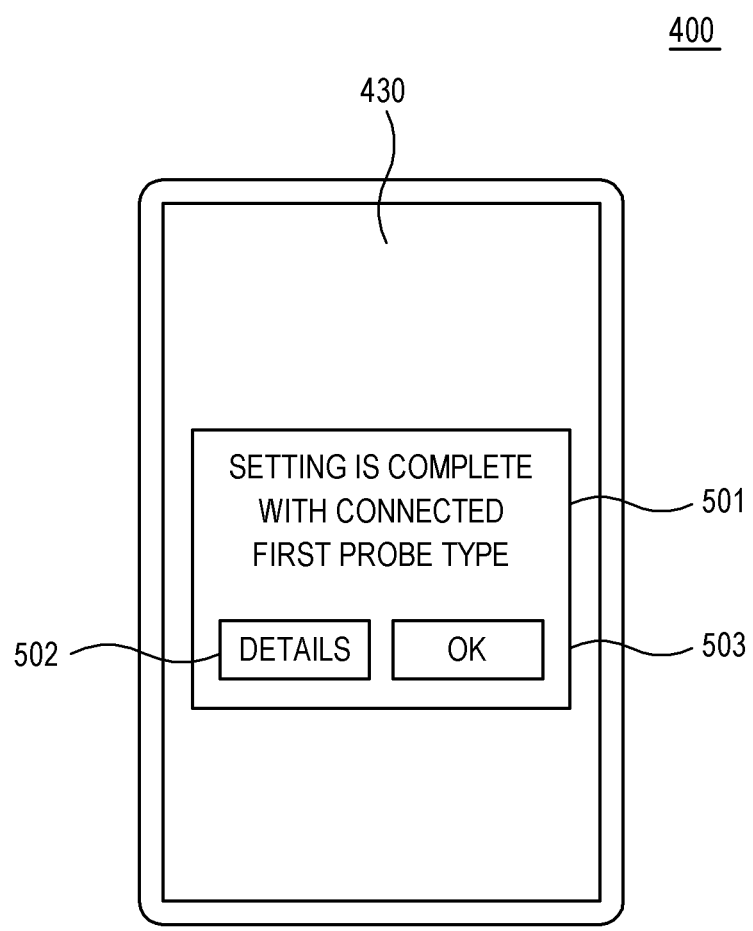
Figure 19:
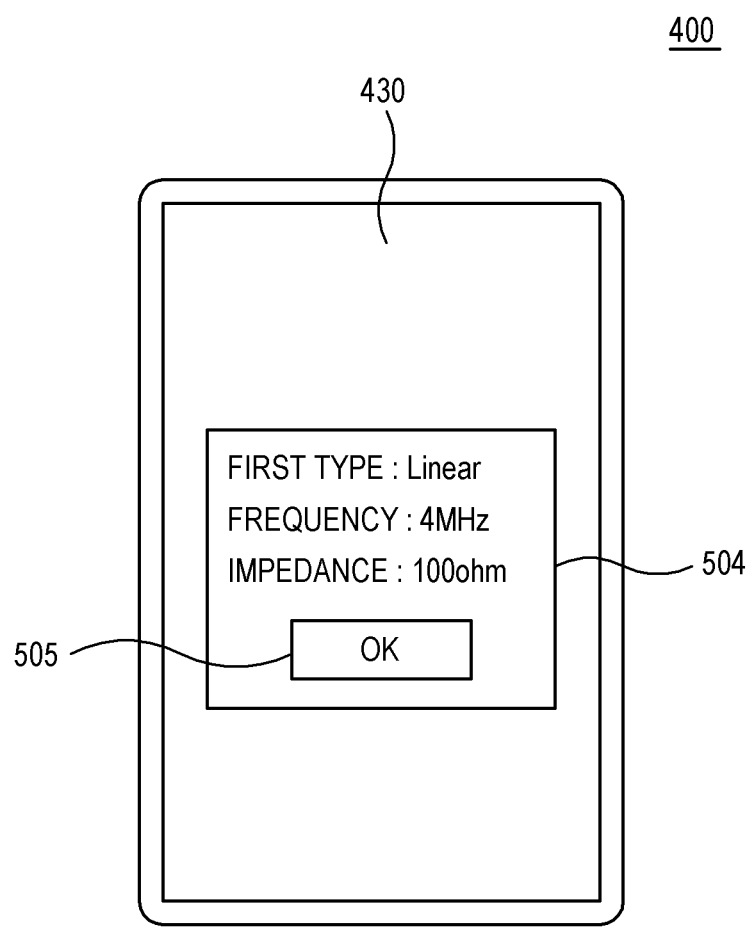

FIGS. 18 and 19 show examples of notifying the probe type information in the probe apparatus 100 according to one embodiment of the present disclosure.

In one exemplary embodiment, the processor 310 of the probe apparatus 100 may determine the probe type corresponding to the transducer array 210 of the head 110 mounted to the main body 120, based on the patterns of the feedback signal responding to the test signal, and controls the display apparatus 400 to display the information about the probe apparatus 100 corresponding to the probe apparatus 100.

Specifically, as shown in FIG. 18, the display 430 of the display apparatus 400 may display a message 501 for informing a user of the determined probe type. To this end, the processor 310 may transmit information about the determined probe type to the display apparatus 400 through the first communicator 350.

The message 501 displayed on the display 430 includes information about the probe type of the transducer array 210 involved in the head 110 connected to the main body 120.

In one exemplary embodiment, the processor 310 may be configured to set a parameter corresponding to the determined probe type, and display the message 501 with the parameter setting results as shown in FIG. 18. When a user selects a detailed information button 502 on the displayed message 501, the display 430 may further display a message 504 involving detailed information about the corresponding probe type as shown in FIG. 19.

When OK buttons 503 and 505 are selected in FIG. 18 and FIG. 19, the displayed messages 501 and 503 disappear, a user is allowed to use the probe apparatus 100 to perform the ultrasound diagnosis, and an ultrasound image corresponding to a diagnosis result is displayed through the display 430 of the display apparatus 400. Here, the processor 410 of the display apparatus 400 may control the displayed messages 501 and 503 to automatically disappear when a predetermined period of time (e.g. five minutes) elapses without a user's clicking to the OK buttons 503 and 505 after the messages 501 and 504 are displayed.

In one exemplary embodiment, the processor 310 transmits the test signal to the transducer array 210 through each of the plurality of channels of the transceiver 320, performs correction of an error between the plurality of channels of the transceiver 320 based on variation in the feedback signal received according to the plurality of channels used in transmitting the test signal, and thus initializes the transceiver 320.

Figures 21A, 21B:
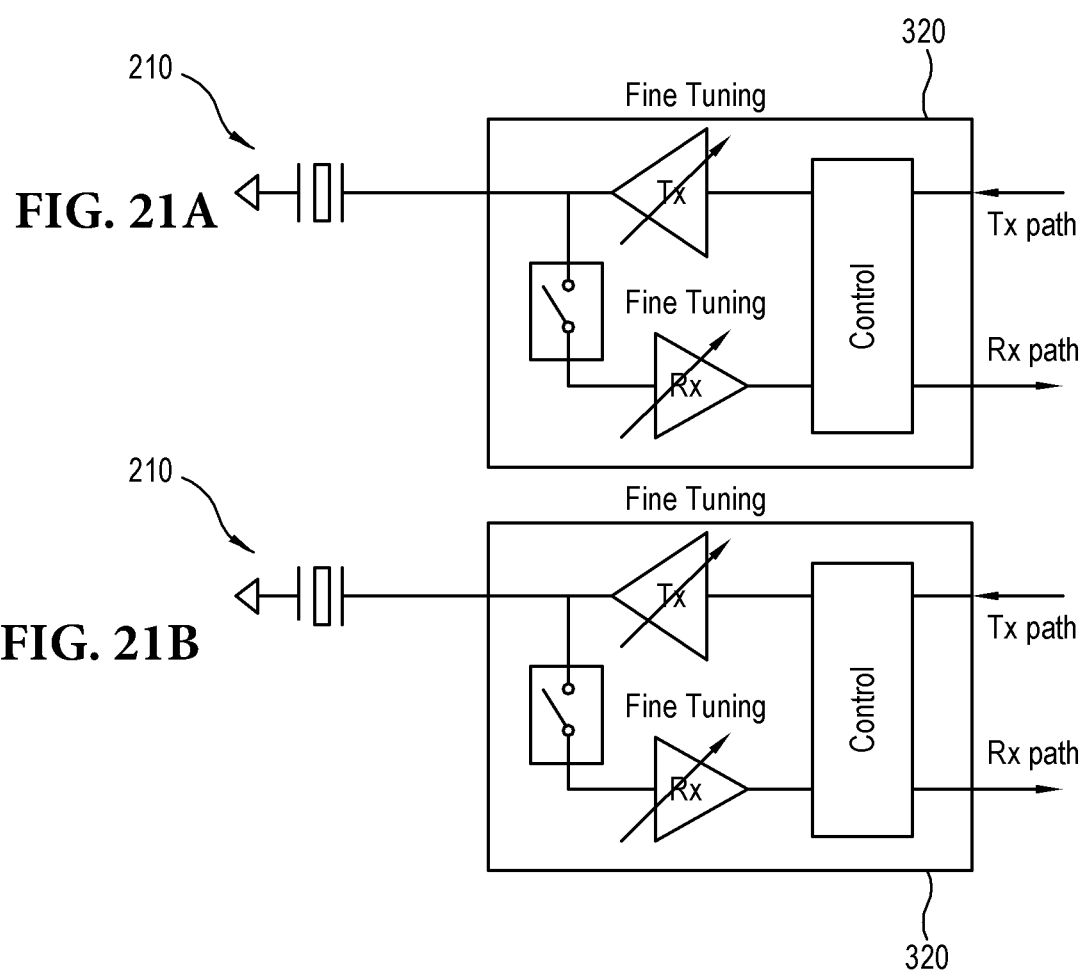
Figure 22:
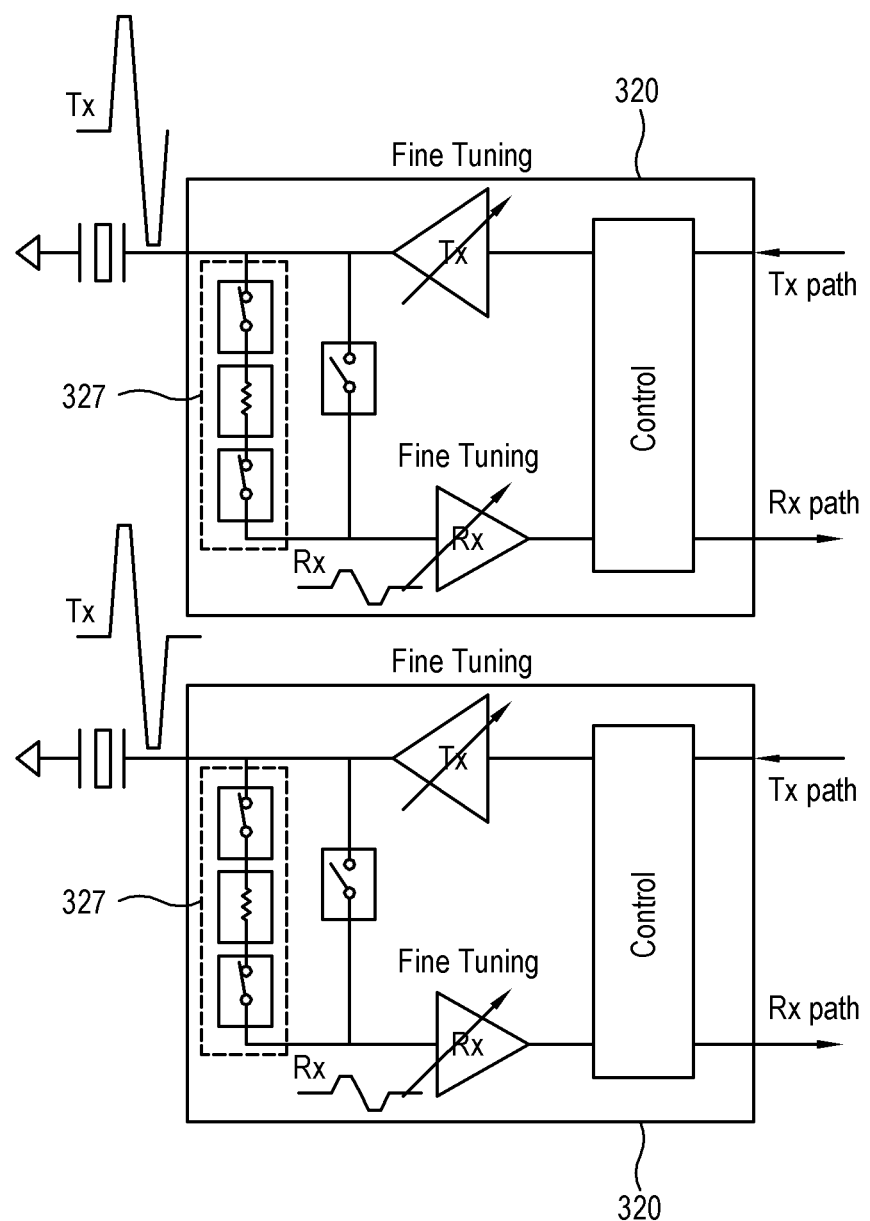

FIGS. 20 to 22 are views for illustrating a procedure of correcting an error between channels in the probe apparatus 100 according to one embodiment of the present disclosure.

In one exemplary embodiment, the processor 310 may sequentially perform (i.e. sweep) transmitting the test signal with regard to each of the plurality of channels of the transceiver 320 and sensing the feedback signal received corresponding to the test signal.

For example, as shown in FIG. 20(*a*), the processor 310 may first transmit the test signal Tx through the first channel C1 and then sense the feedback signals Rx received through other channels C2, C3, C4, . . . , Cn−1, Cn.

Next, as shown in FIG. 20(*b*), the processor 310 may transmit a test signal Tx through the second channel C2 and then sense the freed signal Rx received through other channels C1, C3, C4, . . . , Cn−1, Cn.

As shown in FIG. 20(*c*) and FIG. 20(*d*), the processor 310 may repetitively perform transmitting the test signal and sensing the feedback signal with regard to other channels like the same manner for the first and second channels.

Further, the processor 310 may control the transceiver 320 to correct an error caused between the plurality of channels, using deviation of the feedback signal received in response to the test signal with regard to the channels for transmitting the test signal.

In one exemplary embodiment, when the feedback signal responding to the test signal at a predetermined channel has a deviation higher than a preset reference level as compared with the feedback signals of other channels, the processor 310 may determine that an error occurs in the channel. Here, the processor 310 may determine the deviation of the feedback signal corresponding to each channel, based on the feedback signal received through a predetermined number of adjacent channels (e.g. one, two or three channels).

Further, the channel determined as it has an error is subjected to correction, i.e. fine tuning (hereinafter, referred to as tuning).

In general, there may be difference in performance between channels during a processing procedure in the transceiver 320 and the like chip, and the fine tuning in the present disclosure compensates for the difference in the performance, thereby making the channels keep uniform performance. Here, the fine tuning may include tuning the deviation caused by the transducer 210 itself. Further, the storage 340 may be configured to previously store a reference level for determining whether the error occurs, and data for fine-tuning for each channel.

In one exemplary embodiment, the fine tuning may be performed with regard to the transmission and reception in each channel of the transceiver 320. In FIG. 21, (a) and (b) illustrate that the fine tuning is performed with regard to the transmission and the reception in different channels.

Here, the fine tuning according to channels may be performed with respect to an output amplitude of a transmitted signal, a level of a received (output) signal, a signal to noise (SNR) ratio, etc.

In one exemplary embodiment, the fine tuning is included in a procedure of initializing the transceiver 320. That is, the processor 310 repetitively performs transmitting the test signal to all the channels and receiving the feedback signal responding to the test signal, thereby completing the tuning for the error correction with regard to each channel and performing initialization. Further, the initialized probe apparatus 100 is used in the ultrasound diagnosis.

In one exemplary embodiment, the processor 310 may further perform the fine tuning for the error correction with regard to the channels through the monitoring inside the transceiver 320. FIG. 22(*a*) and FIG. 22(*b*) conceptually illustrate that the fine tuning is performed with regard to each of the transmission and the reception through the internal monitoring in different channels.

To this end, the transceiver 320 may further include a switch 327 for connection with an internal path.

As shown in FIG. 22, when the switch 327 is turned on, the processor 310 controls a second test signal Tx to pass through the inside of the transceiver 320 with regard to each of the plurality of channels, and initializes the transceiver 320 by correction of an error between the plurality of channels based on the deviation of the second test signal Rx received passing through the transceiver 320. Here, the fine tuning using the internal monitoring path is also referred to as calibration.

In one exemplary embodiment, the fine tuning using the internal path may be performed with regard to each of the transmission and the reception according to the channels of the transceiver 320. In FIG. 22, (a) and (b) conceptually illustrate that the fine tuning is performed with regard to each of the transmission and the reception in different channels.

Further, the fine tuning using the internal path may be performed by simultaneously transmitting the second test signal through all the plurality of channels in the transceiver 320, and simultaneously sensing the signals received in response to the second test signal.

By the way, as shown in FIG. 20, the probe apparatus 100 may check the number of channels for the transducer array according to one embodiment of the present disclosure.

Referring to FIG. 20, the processor 310 may further determine whether the channel used in transmitting the test signal among the plurality of channels is connected to the transducer array 210, based on the feedback signal received in response to the test signal for each channel.

In one exemplary embodiment, as shown in FIG. 20, the plurality of channels of the transceiver 320 respectively corresponds to the plurality of elements arranged in the transducer array 210, and the number of elements in the transducer array 210 is lower than or equal to the number of channels.

Alternatively, the number of elements in the transducer array 210 may be equal to or higher than the number of channels in the transceiver 320. In this case, the transceiver 320 is provided in plural, and the sum of all channels in the plurality of transceivers 320 is lower than or equal to the number of elements in the transducer array 210. For example, when the transceiver 320 is a 64-channel ASIC, and the number of elements in the transducer array 214 corresponds to 256 channels, four 64-channel ASICs (chips) may be provided as the transceiver 320. Further, through the channels of the plurality of transceivers 320, it is possible to determine the connection with the transducer array 210.

Thus, at least some of the plurality of channels C1, C2, C3, . . . , Ci−1, Ci, Cn−1, Cn of the transceiver 320 may be connected to the transducer array 210. FIG. 20 illustrates that the channels C1, C2, C3, . . . , Ci−1, Ci are connected to the transducer array 210, and the channels Ci+1, . . . , Cn−1, Cn are not connected to the transducer array 210. Here, in case of the channels Ci+1, . . . , Cn−1, Cn, the feedback signals are not received in response to the test signal transmitted through the channels Ci+1, . . . , Cn−1, Cn since they are not connected to the transducer array 210.

By the foregoing manner, the processor 310 checks, i.e. finds the number of channels in the transducer array 210 and the plurality of channels using the feedback signal. Further, the processor 310 determine whether the plurality of channels and the transducer array 210 are connected or not based on the feedback signal, and cuts off power supplied to at least one channel disconnected from the transducer array 210 among the plurality of channels based on the determination results. For example, in the case of FIG. 20, the channels Ci+1, . . . , Cn−1, Cn among the channels of the transceiver 320 is not supplied with the power by the foregoing procedure of determining the connection. According to another embodiment, the channels not connected to the transducer array 210 may be supplied with power having a lower level than other channels.

In one exemplary embodiment, the processor 310 may determine whether the channel used for transmitting the test signal is connected to the transducer array 210, based on the feedback signal responding to the test signal transmitted through at least some among the plurality of channels.

Specifically, referring to FIG. 20, the processor 310 may sense whether the feedback signal is received in response to the test signal transmitted through the channel Ci+1 among the plurality of channels. When the feedback signal is not received through the channel Ci+1, the processor 310 may determine that the channel and the subsequent channels, i.e. the channels Ci+1, Ci+2, . . . , Cn−1, Cn are not connected to the transducer array 210.

The channel number corresponding to the test signal used in determining the connection with the transducer array 210 may be previously set by the elements of the transducer array 210 and the transceiver 320 and stored in the storage 340.

In one exemplary embodiment, the processor 310 may determine whether each channel and the transducer array 210 are connected or not, based on the feedback signal on the test signal transmitted through a preset number of channels, e.g. three channels Ci, Ci+1, Ci+2. That is, it will be appreciated that the present disclosure may include even the case where feedback signals received through some channels are used to determine whether each channel and the transducer array 210 are connected or not, without using the feedback signals received through all the channels used in transmitting the test signal.

Further, in one exemplary embodiment, the processor 310 may recognize the number of transducer arrays 210 through the foregoing internal monitoring path. That is, as shown in FIG. 22, the processor 310 controls the second test signal Tx to pass through the inside of the transceiver 320 with regard to each of the plurality of channels when the switch 327 is turned on, and uses the second test signal Rx received through the transceiver 320, thereby determining whether the elements of the transducer array 210 are connected with regard to each of the plurality of channels. Thus, the connection determination based on the internal path may be performed in a manner of simultaneously transmitting the second test signal through all the plurality of channels of the transceiver 320, and simultaneously sensing the signal received in response to the transmitted test signal.

By the way, the processor 310 controls the transceiver 320 to transmit the test signal to the transducer array 210 through each of the plurality of channels, and employs the feedback signal received with regard to each of the plurality of channels, thereby detecting whether the elements of the transducer array 210 connected to the plurality of channels are damaged (or broken, used up, etc.).

Figure 23A:
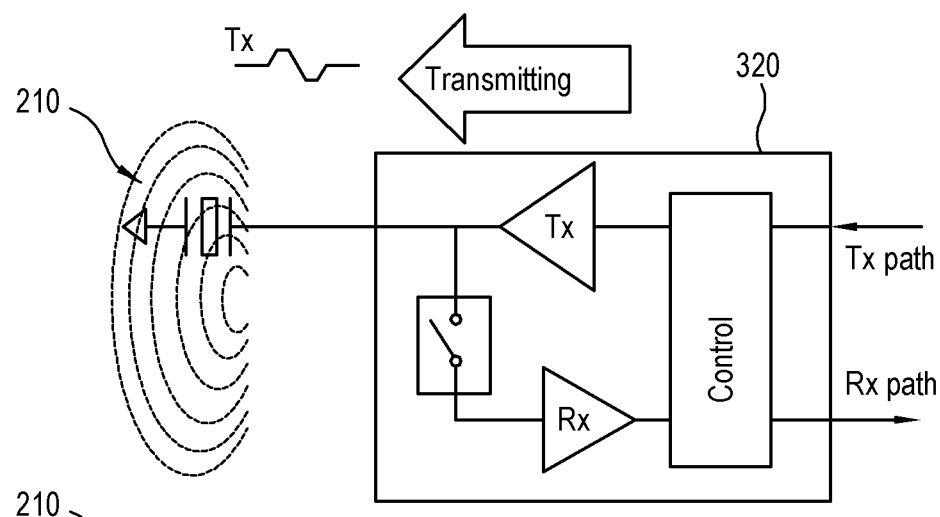
FIGS. 23A, 23B, and 24 are views for illustrating a procedure of detecting whether elements of the transducer array are damaged or not in the probe apparatus according to one embodiment of the present disclosure.
Figure 23B:
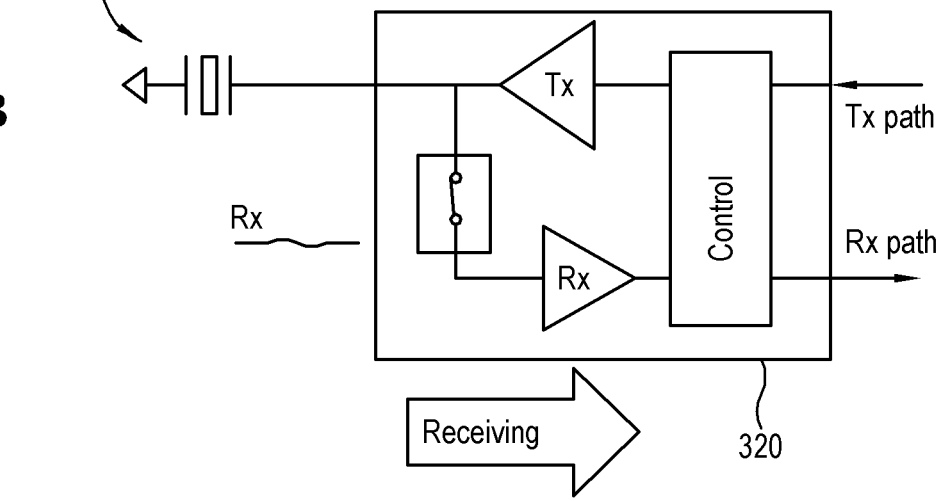
Figure 24:
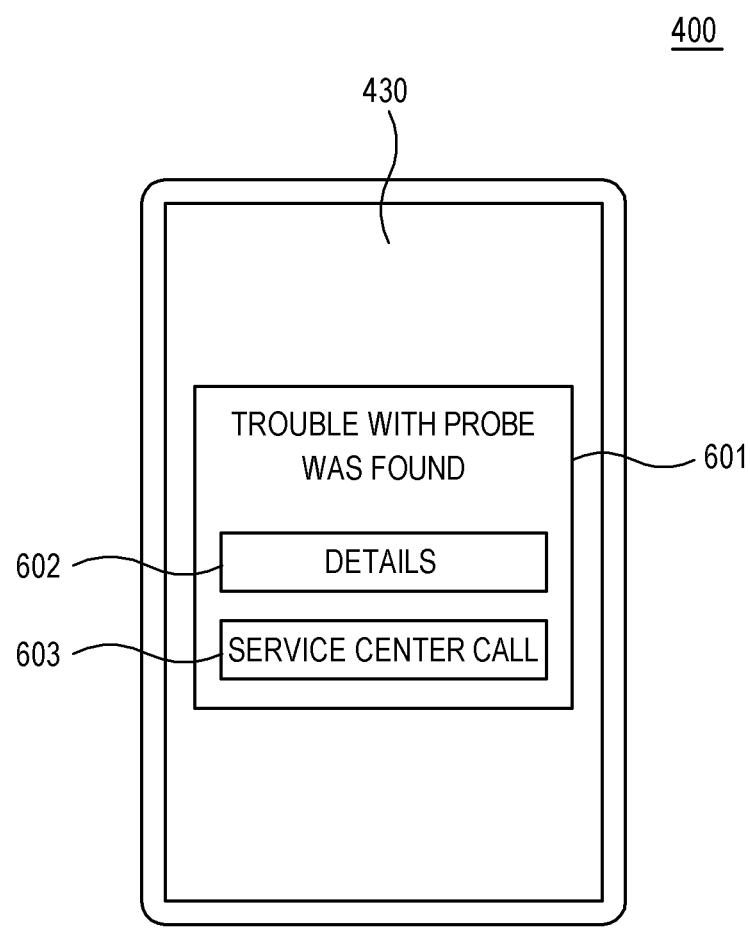

FIGS. 23 and 24 are views for illustrating a procedure of detecting whether the elements of the transducer array 210 are damaged or not in the probe apparatus 100 according to one embodiment of the present disclosure. Here, (a) and (b) of FIG. 23 conceptually illustrate detection of whether the elements respectively corresponding to the channels are damaged or not.

As shown in (a) of FIG. 23, the processor 310 transmits the test signal through each of the plurality of channels of the transceiver 320. Further, referring to (b) of FIG. 23, the transceiver 320 is controlled to receive a feedback signal in response to the test signal transmitted through the plurality of channels.

Here, an abnormal feedback signal may be received with regard to the test signal corresponding to a certain channel among the plurality of channels of the transceiver 320. As shown in (b) of FIG. 23, the abnormal feedback signal may be for example caused when a signal having a remarkably low level is received as compared with the feedback signals of other channels or when no feedback signal is received through a specific channel. As another example, the abnormal feedback signal may be caused when the element corresponding to the transmission may be damaged and thus the feedback signal may be not generated around the damaged element. Further, the abnormal feedback signal may be caused when the feedback signal are not overall generated.

When there is a channel though which the abnormal feedback signal is received with respect to the test signal, the processor 320 may determine that the element of the transducer array 210 is damaged corresponding to the channel.

When it is detected by the foregoing procedure that an element of the transducer array 210 of the transducer array 210 corresponding to a specific channel is damaged, the processor 310 may notify a user of the damage.

Specifically, as shown in FIG. 24, the processor 310 may control the first communicator 350 to send the display apparatus 400 a message 601 for notifying the information about the probe apparatus 100 corresponding to the determined result through the display 430.

A user may click a detail button 602 in the message 601 displayed on the display 430 of the display apparatus 400, and check detailed damage information. The processor 410 of the display apparatus 400 may control the display 430 to display a message for informing that the damaged element has to be replaced or repaired in accordance with a user's selection of the detail button 602. Here, the displayed message may further display information about a position (or the numeral) of the damaged element, a cause of the damage (e.g. expired, etc.) and the like information.

Further, as shown in FIG. 24, the message 601 may further include a service center call button 603. The processor 410 of the display apparatus 400 may automatically contact the service center in response to a user's selection of the service center call button 603, and control the second communicator 450 to make a request for an after-sales service or follow-up service for the probe apparatus 100. Here, the after-sales service may include a remote diagnosis for the probe apparatus 100.

In one exemplary embodiment, the information about the position (or the number) of the damaged element, the cause of the damage (e.g. expired, etc.) and the like information may be transmitted to the service center in response to a user's selection of the service center call button 603, and thus a more efficient service can be provided.

By the way, the processor 310 detects the level of the feedback signal received in response to the test signal, determines impedance Z of the transducer array 210 based on the detected signal level, and adjusts a level of power supplied to the transducer array 210 so as to be matched with the determined impedance Z.

Figure 25A:
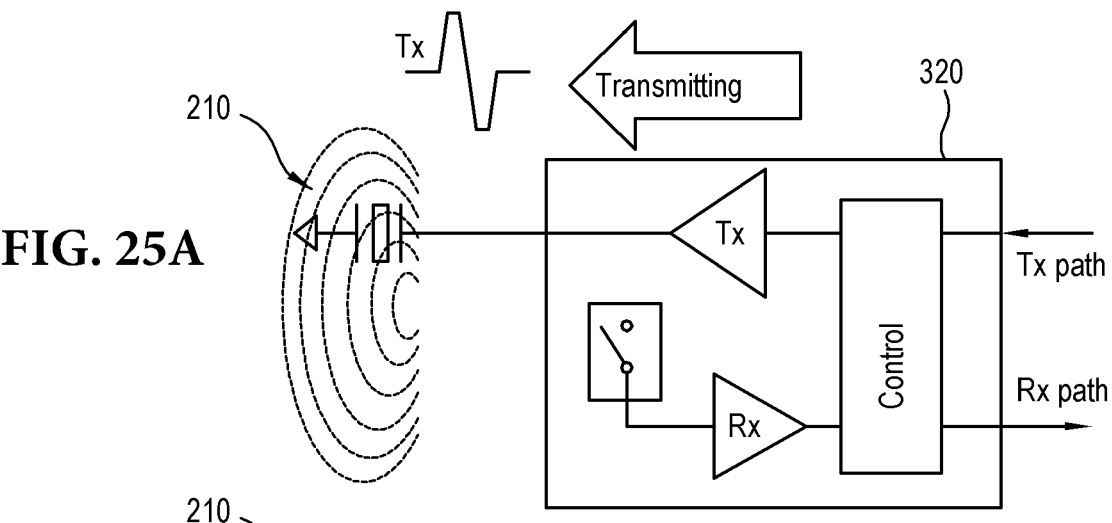
Figure 25B:
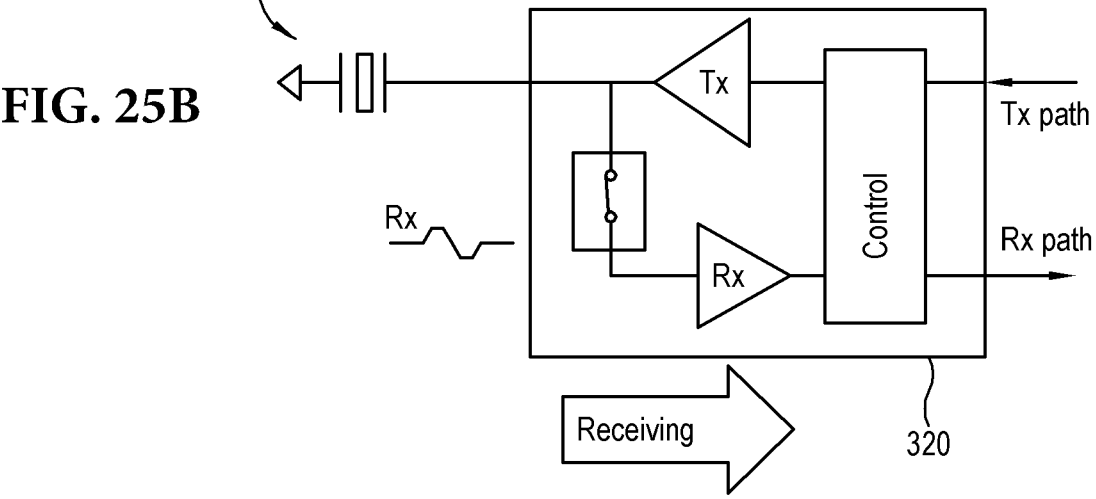

FIGS. 25 and 26 are views for illustrating a procedure of adjusting a power level based on the impedance of the transducer array 210 in the probe apparatus 100 according to one embodiment of the present disclosure.

The processor 310 may determine the impedance of the transducer array 210 by detecting the level of the feedback signal received in response to the test signal of each channel, i.e. an average value of the feedback signal levels.

In general, the transducer array 210 has various values of impedance in accordance with the probe types. Further, even in case of the same kind of probe type, for example, the linear probe, the impedance may vary depending on the materials, arranged shape, size, intervals, etc. of the elements, and therefore the level of supplied power has to be controlled corresponding to the actually measured impedance. The measured impedance is varied in value depending on frequency bands of the signal.

In general, the existing probe apparatus is basically set with extremely high power regardless of actual impedance, thereby causing wasteful power consumption, straining the operation of the device, and laying a high burden on additional heat radiation in terms of the system.

According to one embodiment of the present disclosure, the power supplied to the transducer array 210 is not fixed to a specific level, but controlled to have an optimized level (e.g. acoustic power) corresponding to the impedance of the mounted transducer array 210. For example, when the impedance is high, the power may be set to have a low level. When the impedance is low, the power may be set to have high level.

FIG. 25 illustrates that the feedback signal Rx received in response to the test signal Tx is low, and FIG. illustrates that the feedback signal Rx received in response to the test signal Tx is high.

As shown in (b) of FIG. 25, when the feedback signal has a low level, the power level may be adjusted in a manner of increasing the level of the power supplied to the transducer array 210 at a predetermined rate. Further, as shown in (b) of FIG. 26, when the feedback signal has a high level, the power level may be adjusted in a manner of decreasing the level of the power supplied to the transducer array 210.

To this end, the storage 340 may be configured to store information about the power level corresponding to detected impedance. Further, the processor 310 may determine whether to adjust the power level by comparison between the detected impedance and a reference value, and the reference value may be also stored in the storage 340.

As described above, the probe apparatus 100 according to one embodiment of the present disclosure is configured to control the power level in accordance with the impedance. Therefore, it is basically possible to make the device operate with low power, and it is possible to supply power optimized to the operations by further adjusting the overall power level even when the power level is slightly high or low after completing parameter setting for the operation.

Below, a method of controlling the probe apparatus 100 according to the embodiments of the present disclosure will be described with reference to the accompanying drawings.

Figure 27:
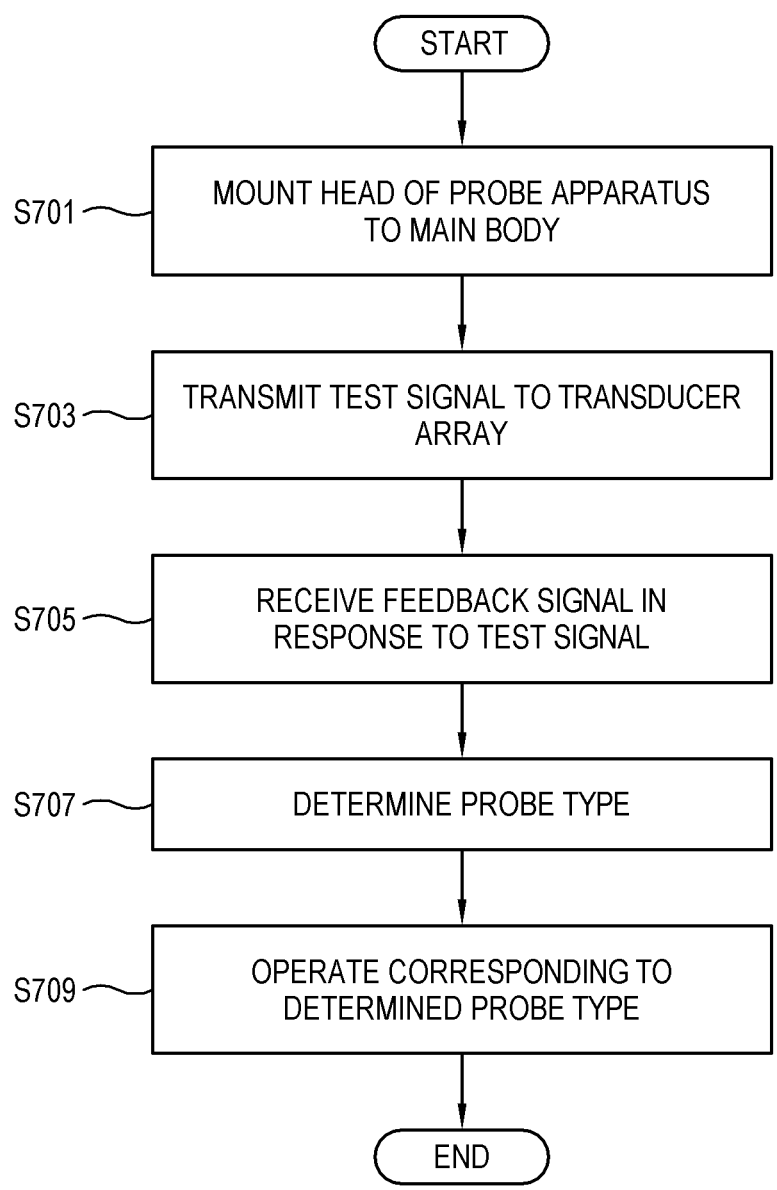
FIG. 27 is a flowchart of illustrating a method of controlling the probe apparatus according to one embodiment of the present disclosure.

FIG. 27 is a flowchart of illustrating a method of controlling the probe apparatus according to one embodiment of the present disclosure.

As shown in FIG. 27, in the probe apparatus 100 for outputting an ultrasound signal to the object according to one embodiment, the head 110 is mounted to the main body 120 (S701). Here, in the probe apparatus 100 described with reference to FIG. 3 and FIG. 4, the head 110 may be detachably provided in the main body 120. As described with reference to FIGS. 5 to 8, the head 110 is provided in plural (e.g. 111, 112 and 113) corresponding to the probe types of the transducer array 210, and one among the plurality of heads 111, 112 and 113 may be mounted to the main body 120 in accordance with diagnosis targets, a user's use purpose, etc.

The processor 310 of the probe apparatus 100 transmits a predetermined test signal to the transducer array 210 (S703). Here, the processor 310 may control the transceiver 320 to transmit the test signal to the transducer array 210 in the head 110 when it is sensed that the head 110 is coupled to the main body 120.

In one exemplary embodiment, the transceiver 320 includes a plurality of channels capable of transceiving a signal, and the transceiver 320 may transmit the test signal through one channel among the plurality of channels.

The transceiver 320 receives a feedback signal from the transducer array 210 in response to the test signal transmitted in the operation S703 (S705). Here, the transceiver 320 may receive an interference signal, received through the channels except the channel used in transmitting the test signal in the operation S703 among the plurality of channels, as the feedback signal.

The processor 310 determines the probe type corresponding to the transducer array 210 of the head 110 mounted in the operation S701 based on the feedback signal received in the operation S705 (S707). Here, the processor 310 may determine the probe type based on the level change in the feedback signal received through each of the plurality of channels in sequence from the channel adjacent to the channel used in transmitting the test signal.

The probe type corresponds to the element arrangement of the transducer array 210, and the probe type may be variously provided in accordance with a diagnosis target (e.g. a body part), a diagnosis purpose, etc. like a linear type, a convex type, a phased type, etc.

The processor 310 controls the probe apparatus 100 to operate in accordance with the types determined in the operation S707 (S709). Here, the processor 310 may set a parameter for operations of the probe apparatus 100 corresponding to the probe type determined in the operation S707, and a user may be notified of the setting results through the display apparatus 400 as shown in FIG. 18. Further, the storage 340 of the probe apparatus 100 may be configured to store information corresponding to the probe type of the plurality of heads 110 mountable to the main body 120, and the processor 310 may load information corresponding the determined probe type from the storage 340 and set the parameter.

By the way, in the operation S707 according to one embodiment, the processor 310 may initialize the transceiver 320 by correcting an error between the plurality of channels, based on the feedback signal received in the operation S705. Here, the processor 310 may perform fine tuning for correcting the error based on the deviation of the feedback signal received according to the plurality of channels used in transmitting the test signal, and perform more accurate fine tuning based on the second test signal passing through the inside of the transceiver 320.

Further, in the operation S707 according to one embodiment, the processor 310 determines whether the plurality of channels and the transducer array 210 are connected or not based on the feedback signal received in the operation S705, and cuts off power supplied to at least one channel among the plurality of channels based on the determination results. Here, the processor 310 may determine whether the channel used in transmitting the test signal and the element of the transducer array 210 are connected or not in the operation S703, using the feedback signal received in the operation S705 in response to the test signal transmitted through at least some among the plurality of channels. Further, it is possible to determine whether the element of the transducer array 210 and each channel, based on the second test signal passing through the inside of the transceiver 320.

Further, in the operation S707 according to one embodiment, the processor 310 may detect whether the element of the transducer array 210 connected to each of the plurality of channels is damaged, based on the feedback signal received in the operation S705.

Further, in the operation S707 according to one embodiment, the processor 310 detects the level of the feedback signal received in the operation S705, determines the impedance of the transducer array 210 based on the detected signal level, and adjusts the level of the power supplied to the transducer array 210 corresponding to the determined impedance.

A user may be notified of the results from the procedures performed in the operation S707, and for example a predetermined message may be displayed through the display 430 of the display apparatus 400 communicable with the probe apparatus 100. Here, a notification method for a user is not limited to the message using the display apparatus 400. For example, peripheral apparatuses including the probe apparatus 100 or the display apparatus 400 may be used to output a predetermined signal, and the kind of message or signal may be variously realized in accordance with notification purposes.

According to the foregoing embodiments of the present disclosure, the head 110 including the transducer array 210 of various probe types is mountable to the main body 120, and the probe apparatus 100 is automatically set to have a parameter for operation corresponding to the mounted probe type.

The features according to the embodiments of the present disclosure may be partially or wholly coupled or combined, and technically variously interworked and driven as fully appreciated by those skilled in the art. Further, the exemplary embodiments may be materialized independently of each other or realized to interwork together.

Thus, according to one embodiment of the present disclosure, there is provided an ultrasound probe apparatus which can automatically recognize a probe type and operate according to the recognized probe types. Therefore, the head of various types is connected to the main body in accordance with diagnosis purposes.

Further, the parameter is automatically set in accordance with the determined probe types, and thus a user does not have to manually input setting values, thereby more improving user convenience.

Further, the test signal is transmitted using the plurality of channels of the transceiver, and the feedback signal received in response to the test signal is used in recognizing the probe type, thereby automatically optimizing an operation to the mounted probe type without additional parts or costs.

Further, the test signal may be variously utilized in measuring the impedance of the transducer array, recognizing the number of array elements, determining about whether the transducer is damaged, characteristic compensation according to the channels of the transceiver, etc.

By the way, the foregoing exemplary embodiments of the present disclosure may be realized by a computer readable recording medium. The computer-readable recording medium includes a storage medium for storing data readable by a transmission medium and a computer system. The transmission medium may be materialized by a wired/wireless network where computer systems are linked.

The foregoing exemplary embodiments may be realized by hardware and combination between hardware and software. As the hardware, the processor 310 or 410 may include a nonvolatile memory in which a computer program is stored as the software, a RAM in which the computer program stored in the nonvolatile memory is loaded, and a CPU for executing the computer program loaded in the RAM. The nonvolatile memory may include a hard disk drive, a flash memory, a ROM, CD-ROMs, magnetic tapes, a floppy disc, an optical storage, a data transfer device using Internet, etc., but is not limited thereto. The nonvolatile memory is a kind of computer-readable recording medium in which a program readable by a computer of the present disclosure is recorded.

The computer program is a code that is read and executed by the CPU, and includes codes for performing the operations of the processor 310 such as the operations S701 to S709 as shown in FIG. 27.

The computer program may be included in an operating system provided in the probe apparatus 100 or the display apparatus 400, or software including an application and/or software interfacing with an external device.

Although the present disclosure has been shown and described through exemplary embodiments, the present disclosure is not limited to the exemplary embodiments and may be variously materialized within the appended claims.

What is claimed is:

1. A probe apparatus comprising:
   a main body; and
   a head detachably connected to the main body, and comprising a transducer array configured to output ultrasound signals,
   the main body comprising:
      a transceiver configured to transmit and receive signals to and from the transducer array through a plurality of channels; and
      at least one processor configured to:
         control the transceiver to transmit a test signal to the transducer array of the head through a channel among the plurality of channels,
         control the transceiver to receive respective first feedback signals corresponding to the transmitted test signal on the plurality of channels,
         identify a signal level pattern of signal levels of the respective first feedback signals on the plurality of channels, the signal level pattern being identified based on rates of change of the signal levels of the respective first feedback signals on the plurality of channels and being identified from among a plurality of signal level patterns each corresponding to a one of plurality of different probe types of the transducer array,
         identify a probe type of the transducer array among the plurality of different probe types based on the identified signal level pattern, and
         control operations of the probe apparatus based on the identified probe type.

2. The probe apparatus according to claim 1, wherein the at least one processor is configured to set a parameter for controlling the operations of the probe apparatus based on the identified probe type.

3. The probe apparatus according to claim 1,
wherein the transceiver is configured to transmit the test signal through a first channel among the plurality of channels, and
receive the plurality of first feedback signals through channels of the plurality channels other than the first channel.

4. The probe apparatus according to claim 3, wherein the feedback signals are received through channels of the plurality of channels adjacent to the first channel.

5. The probe apparatus according to claim 1, wherein the processor is configured to control the transceiver to sequentially transmit respective test signals to the transducer array through each of the plurality of channels, and initialize the transceiver by correcting error between the plurality of channels based on deviation of a plurality of second feedback signals received based on the sequentially transmitted test signals.

6. The probe apparatus according to claim 1, wherein the processor is configured to determine whether a channel for transmitting the test signal among the plurality of channels is connected or not based on the plurality of first feedback signals, and cut off power supplied to at least one among the plurality of channels based on a result of the determination.

7. The probe apparatus according to claim 1, wherein the plurality of channels correspond to respective elements of the transducer array, and a number of elements in the transducer array is equal to or less than a number of the plurality of channels.

8. The probe apparatus according to claim 1, wherein the processor is configured to detect a level of a feedback signal among the plurality of first feedback signals, determine impedance of the transducer array based on the detected level of feedback signal, and adjust a level of power supplied to the transducer array based on the determined impedance.

9. A medical instrument comprising a probe apparatus and a display apparatus,
the probe apparatus comprising:
a main body, and a head detachably connected to the main body, and comprising a transducer array configured to output ultrasound signals,
the main body comprising:
a transceiver configured to transmit and receive signals to and from the transducer array through a plurality of channels;
at least one processor configured to:
control the transceiver to transmit a test signal to the transducer array of the head through a channel among the plurality of channels,
control the transceiver to receive respective feedback signals corresponding to the transmitted test signal on the plurality of channels,
identify a signal level pattern of signal levels of the respective feedback signals on the plurality of channels, the signal level pattern being identified based on rates of change of the signal levels of the respective feedback signals on the plurality of channels and being identified from among a plurality of signal level patterns each corresponding to one of a plurality of different probe types of the transducer array,
identify a probe type of the transducer array among the plurality of different probe types based on the identified signal level pattern, and
control operations of the probe apparatus based on the identified probe type; and communication circuitry configured to communicate with the display apparatus and transmit information to the display apparatus about reflections by an object of the ultrasound signals, and
the display apparatus comprises a display configured to display an image generated based on the information received from the communication circuitry.

10. A method of controlling a probe apparatus comprising a main body and a head detachably connected to the main body, the method comprising:
determining whether a head comprising a transducer array configured to output ultrasound signals is connected to the main body;
transmitting a test signal to the transducer array through a channel among a plurality of channels of a transceiver provided in the probe apparatus;
receiving respective first feedback signals corresponding to the transmitted test signal on the plurality of channels,
identifying a signal level pattern of signal levels of the respective first feedback signals on the plurality of channels, the signal level pattern being identified based on rates of change of the signal levels of the respective first feedback signals on the plurality of channels and being identified from among a plurality of signal level patterns each corresponding to one of a plurality of different probe types of the transducer array;
identifying a probe type of the transducer array among the plurality of different probe types based on the identified signal level pattern; and
control operations of the probe apparatus based on the identified probe type.

11. The method according to claim 10, further comprising setting a parameter for controlling the operations of the probe apparatus based on the identified probe type.

12. The method according to claim 10, further comprising:
transmitting the test signal through a first channel among the plurality of channels; and
receiving the plurality of first feedback signals through channels of the plurality of channels other than the first channel.

13. The method according to claim 12, wherein the feedback signals are received through channels of the plurality of channels adjacent to the first channel.

14. The method according to claim 10, further comprising:
sequentially transmitting respective test signals to the transducer array, and
correcting error between the plurality of channels based on deviation of a plurality of second feedback signals received based on the sequentially transmitted test signals.

15. The method according to claim 10, further comprising:
determining whether a channel for transmitting the test signal among the plurality of channels is connected or not based on the plurality of first feedback signals; and
cutting off power supplied to at least one among the plurality of channels based on a result of the determination.

16. The probe apparatus according to claim 1, wherein the probe type corresponding to the transducer array of the head is identified to be one of a linear probe, a convex probe, or a phased probe.

17. The medical instrument according to claim 9, wherein the probe type corresponding to the transducer array of the head is identified to be one of a linear probe, a convex probe, or a phased probe.

18. The method according to claim 10, wherein the probe type corresponding to the transducer array of the head is identified to be one of a linear probe, a convex probe, or a phased probe.

* * * * *